United States Patent
Spencer et al.

(10) Patent No.: US 10,359,351 B2
(45) Date of Patent: Jul. 23, 2019

(54) METHOD OF ELECTRICALLY MEASURING THE ELECTRICAL PROPERTIES OF INDIVIDUAL PARTICLES FLOWING IN A LIQUID

(71) Applicant: University of Southampton, Southampton (GB)

(72) Inventors: Daniel Christopher Spencer, Southampton (GB); Hywel Morgan, Southampton (GB)

(73) Assignee: University of Southampton, Southampton (GB)

( * ) Notice: Subject to any disclaimer, the term of this patent is extended or adjusted under 35 U.S.C. 154(b) by 0 days.

(21) Appl. No.: 14/392,103

(22) PCT Filed: Apr. 15, 2014

(86) PCT No.: PCT/GB2014/000147
§ 371 (c)(1),
(2) Date: Oct. 14, 2015

(87) PCT Pub. No.: WO2014/170626
PCT Pub. Date: Oct. 23, 2014

(65) Prior Publication Data
US 2016/0041080 A1     Feb. 11, 2016

(30) Foreign Application Priority Data
Apr. 16, 2013    (GB) ................... 1306913.3

(51) Int. Cl.
*G01N 15/10*     (2006.01)
*G01N 15/00*     (2006.01)

(52) U.S. Cl.
CPC . *G01N 15/1031* (2013.01); *G01N 2015/0053* (2013.01); *G01N 2015/1006* (2013.01); *G01N 2015/1087* (2013.01)

(58) Field of Classification Search
CPC .......................... G01N 15/10; G01N 15/1031
See application file for complete search history.

(56) References Cited

U.S. PATENT DOCUMENTS

| 3,530,713 A | 9/1970 | Nazareth, Jr. |
| 3,944,917 A | 3/1976 | Hogg et al. |

(Continued)

FOREIGN PATENT DOCUMENTS

| EP | 1335198 A1 | 8/2003 |
| EP | 2211164 A1 | 7/2010 |

(Continued)

OTHER PUBLICATIONS

T. Sun et al., High speed multi-frequency impedance analysis of single particles in a microfluidic cytometer using maximum length sequences, Lab on a Chip, vol. 7, pp. 1034-1040 (published Jun. 8, 2007).*

(Continued)

*Primary Examiner* — Matthew G Marini
*Assistant Examiner* — Quang X Nguyen
(74) *Attorney, Agent, or Firm* — Iandiorio Teska & Coleman, LLP

(57) ABSTRACT

A method of electrically measuring the electrical properties of individual particles flowing in a liquid, which method comprises: (i) providing apparatus (3) which is for electrically measuring the individual particles and which has: (a) a fluidic channel (5) for receiving a liquid (6) having the individual particles (4) in suspension in the liquid (6); (b) a first electrode arrangement (8) having at least one measurement electrode (16) and at least one signal electrode (11); and (c) at least one other electrode arrangement (9) having at least one measurement electrode (18) and at least one signal electrode (13); (ii) providing a flow of the liquid (6) through the fluidic channel (5); (iii) applying a first electrical (Continued)

Block diagram to perform measurement for standard guard electrode design.

signal through the liquid (6) and along a first conduction path between the measurement electrode (16) and the signal electrode (11) of the first electrode arrangement (8); (iv) applying an electrical signal through the liquid (6) and along at least one other conduction path; (v) comparing the electrical signal between the first and the other conduction paths to generate a comparison signal; (vi) detecting an individual particle passing through the apparatus (3) by detecting a feature of the comparison signal of the individual particle, and obtaining at least one output waveform; (vii) measuring a height-related feature of the output waveform of the individual particle, and generating a first order assessment of the electrical properties of the individual particle; and (viii) assessing the shape of the output waveform to perform a second order adjustment to the first order assessment of the electrical properties of the individual particle, with the second order adjustment utilising data on a perceived degree of error in the first order assessment based on information on a known relationship between the waveform shape and the error in the first order assessment.

20 Claims, 30 Drawing Sheets

(56) References Cited

U.S. PATENT DOCUMENTS

| | | |
|---|---|---|
| 4,751,842 A | 6/1988 | Ekrann et al. |
| 5,436,565 A | 7/1995 | Gammell |
| 6,426,615 B1 | 7/2002 | Mehta |
| 2003/0102854 A1 | 6/2003 | Gascoyne et al. |
| 2008/0111563 A1 | 5/2008 | Ott et al. |
| 2010/0006441 A1 | 1/2010 | Renaud et al. |
| 2011/0031389 A1 | 2/2011 | Reed et al. |
| 2012/0084022 A1* | 4/2012 | Giovangrandi ........... G01F 1/58 702/45 |
| 2013/0175171 A1 | 7/2013 | Aizel et al. |
| 2015/0102822 A1 | 4/2015 | Okuda |
| 2016/0041081 A1 | 2/2016 | Spencer et al. |
| 2016/0059206 A1 | 3/2016 | Chen et al. |

FOREIGN PATENT DOCUMENTS

| | | |
|---|---|---|
| EP | 2259044 A1 | 12/2010 |
| WO | WO 97/15825 | 5/1997 |
| WO | WO 03/048728 A2 | 6/2003 |
| WO | WO2007/088517 A2 | 8/2007 |

OTHER PUBLICATIONS

Barat et al., "Simultaneous High Speed Optical and Impedance Analysis of Single Particles With a Microfluidic Cytometer", Lab On A Chip, The Royal Society of Chemistry, 2012, 12, 118, pp. 118-126.

Spencer et al., "Positioning Dependence of Particles in Microfluidic Impedance Cytometry", Lab On A Chip, The Royal Society of Chemistry, 2011, 11, pp. 1234-1239.

Lanz et al., "Differential Impedance Spectrometer And Vision System For Analysis of Single Cells", IEEE, Transducers 2009, Denver, CO, USA, Jun. 21-25, 2009, pp. 1297-1300.

* cited by examiner

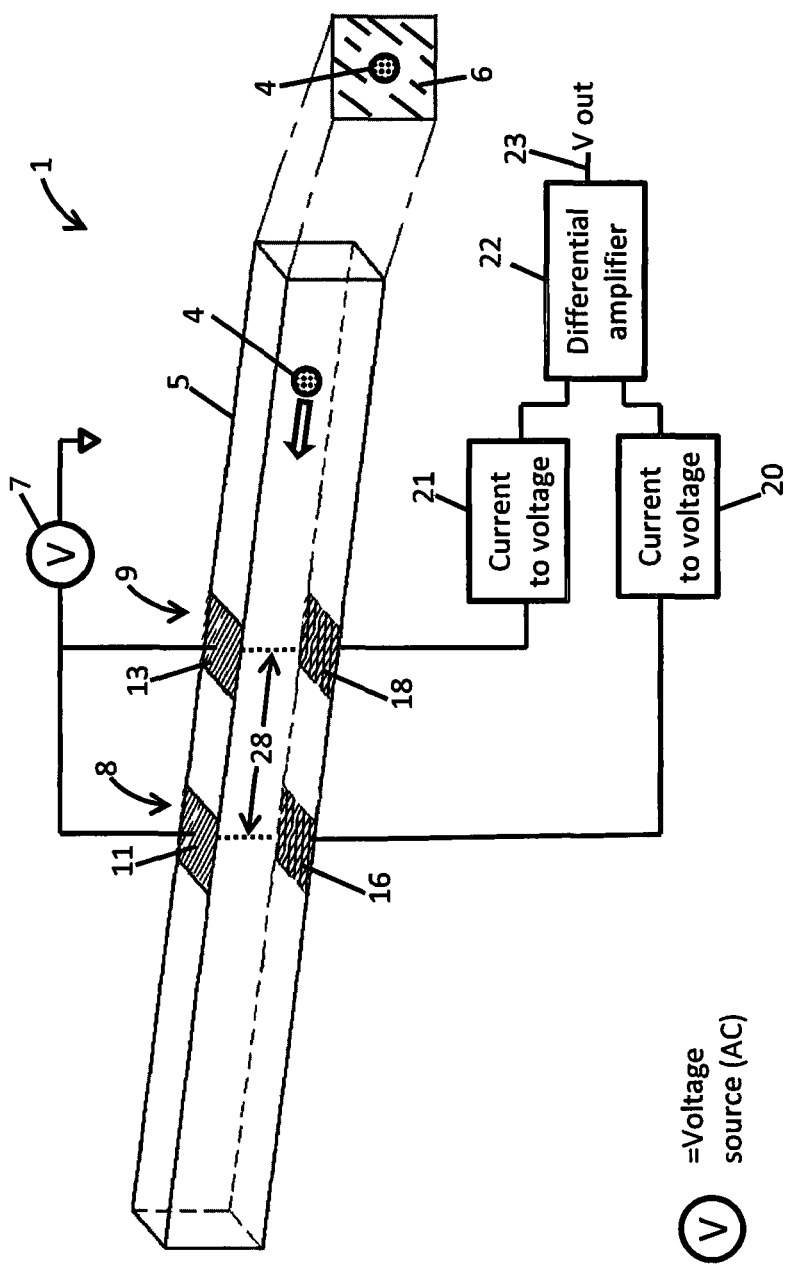
Figure 1. Block diagram to perform measurement for standard 4 electrode design.

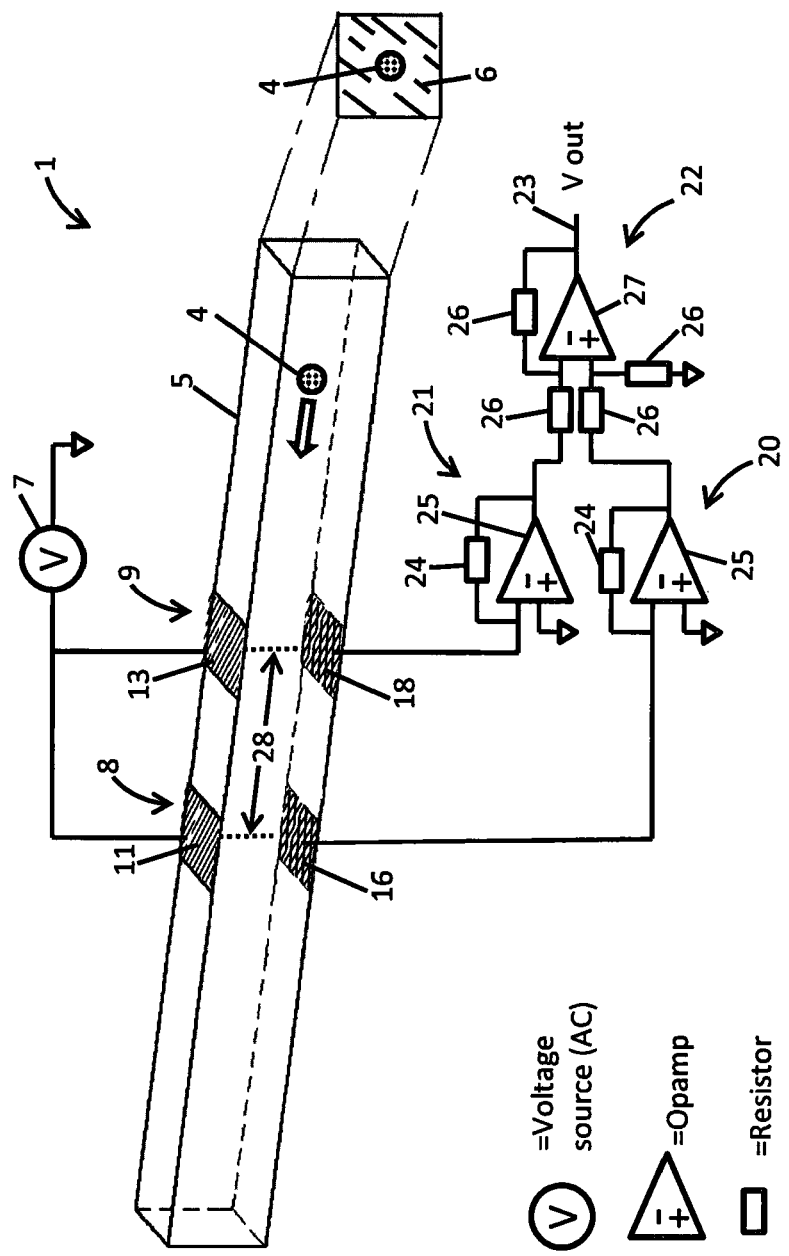
Figure 2. Circuit diagram to perform measurement for standard 4 electrode design.

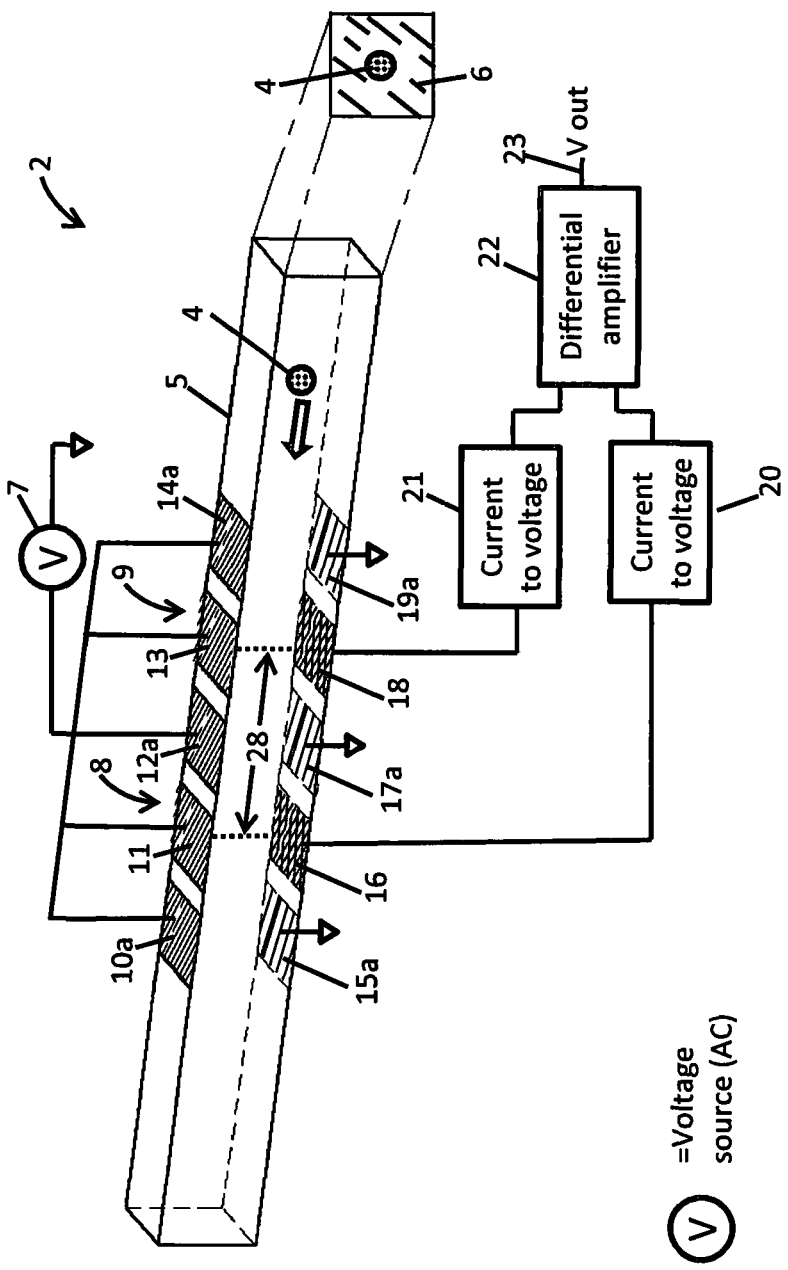
Figure 3. Block diagram to perform measurement for standard guard electrode design.

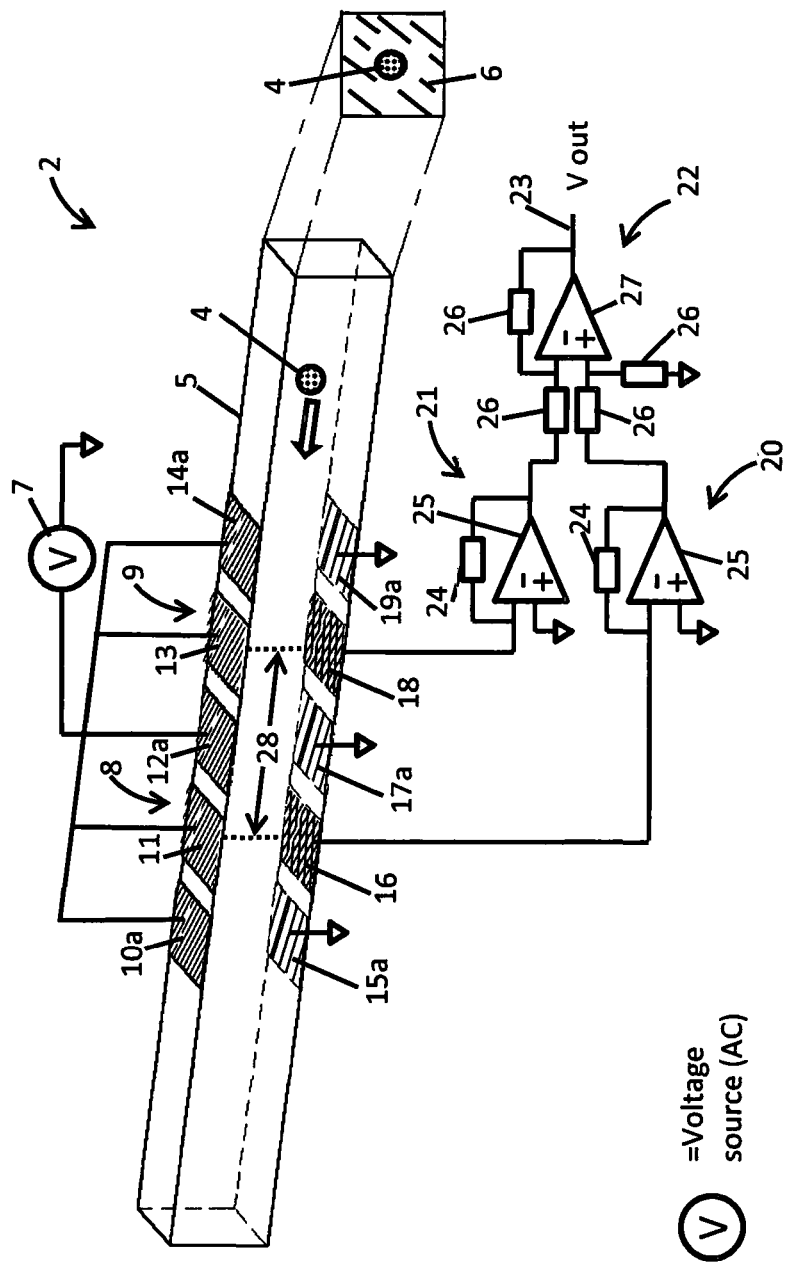
Figure 4. Circuit diagram to perform measurement for standard guard electrode design.

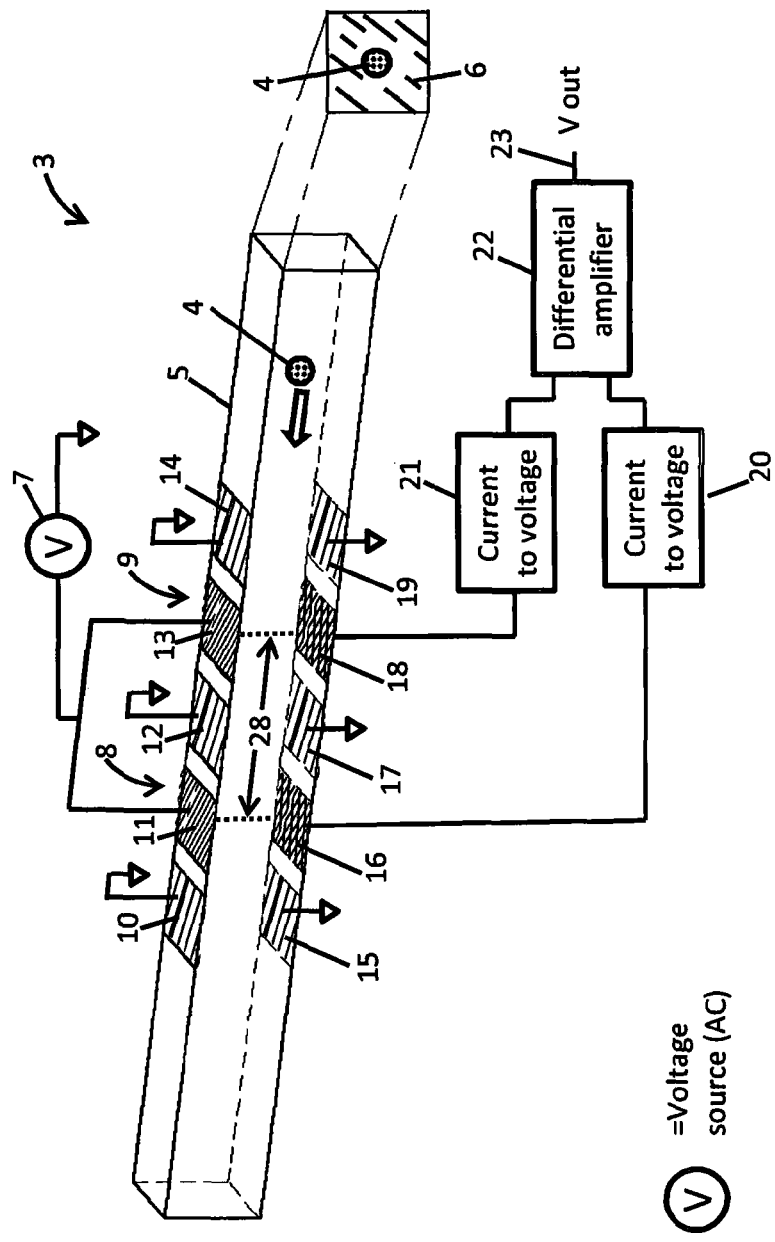
Figure 5. Block diagram to perform measurement for new electrode design.

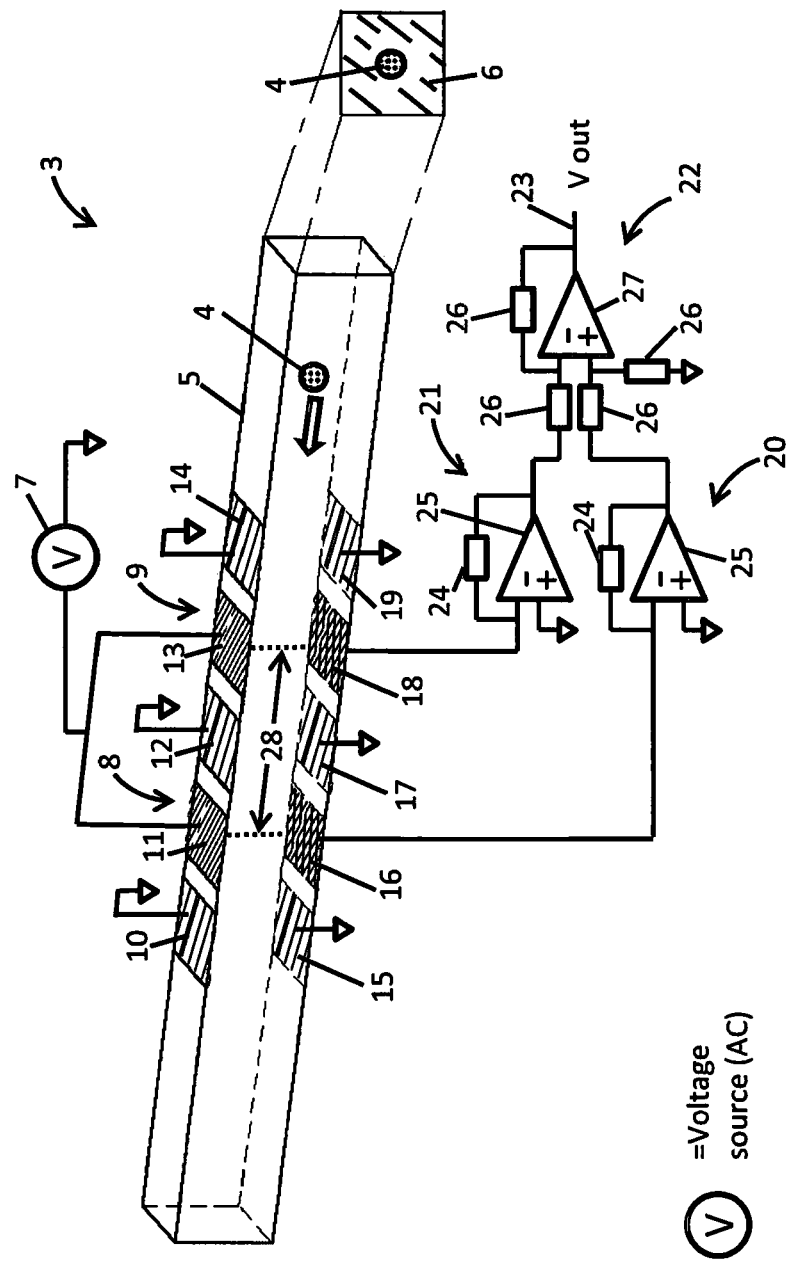
Figure 6. Circuit diagram to perform measurement for new electrode design.

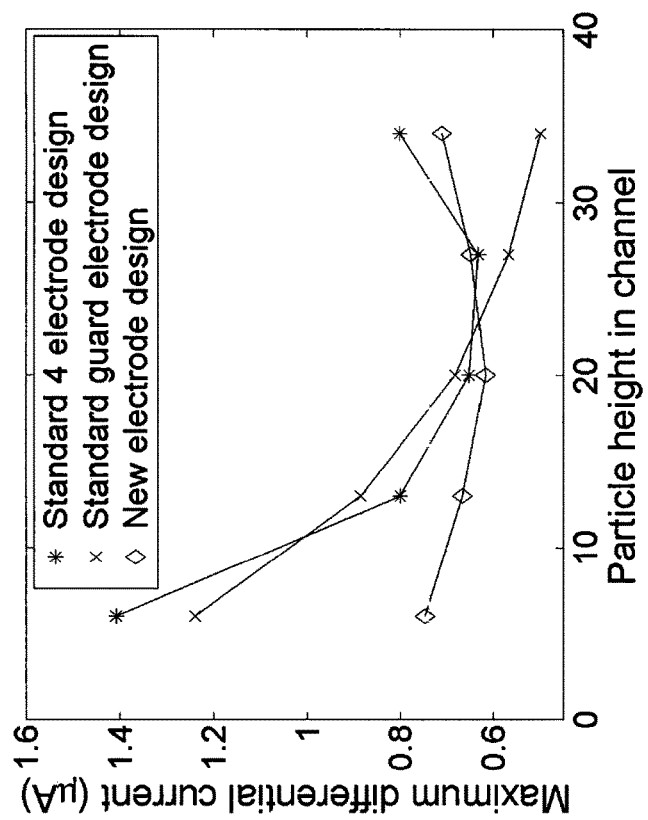
Figure 7. Simulated variation in differential current (impedance signal) with particle height for the 3 electrode designs shown in Figures 1-6.

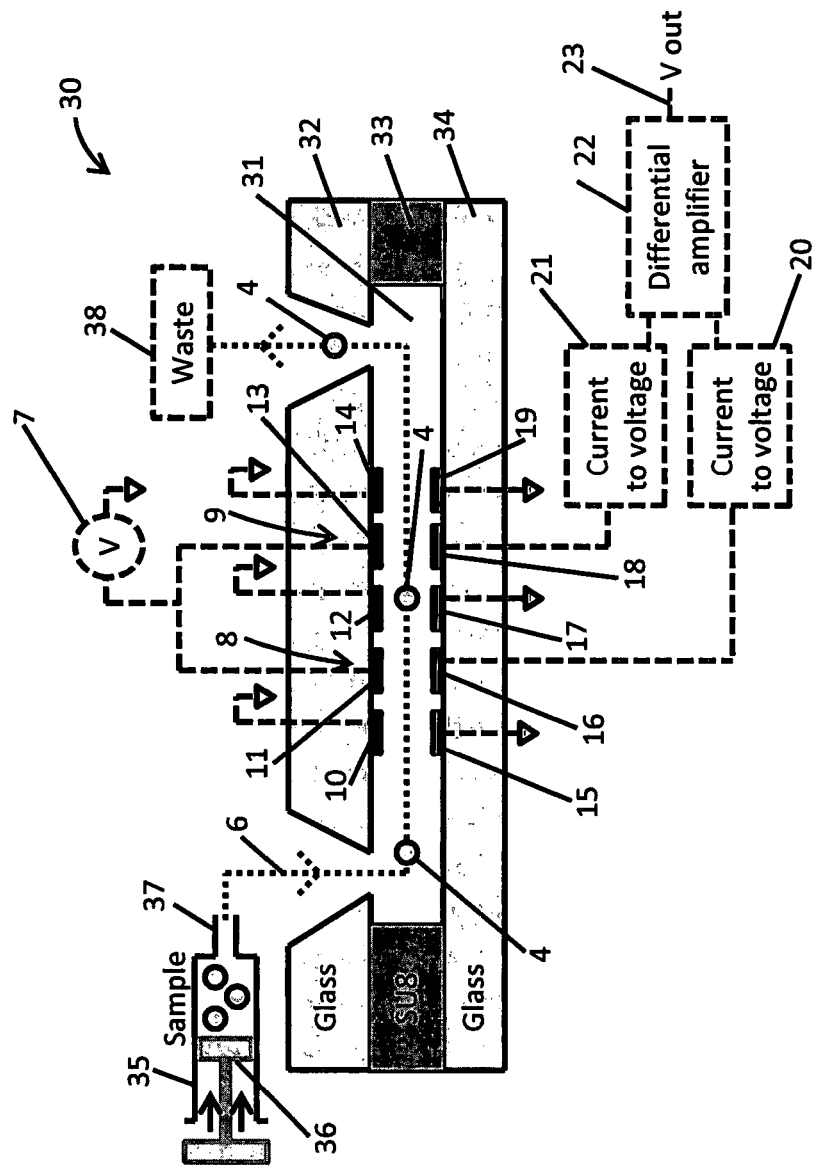
Figure 8. Overview of operation of the new electrode design.

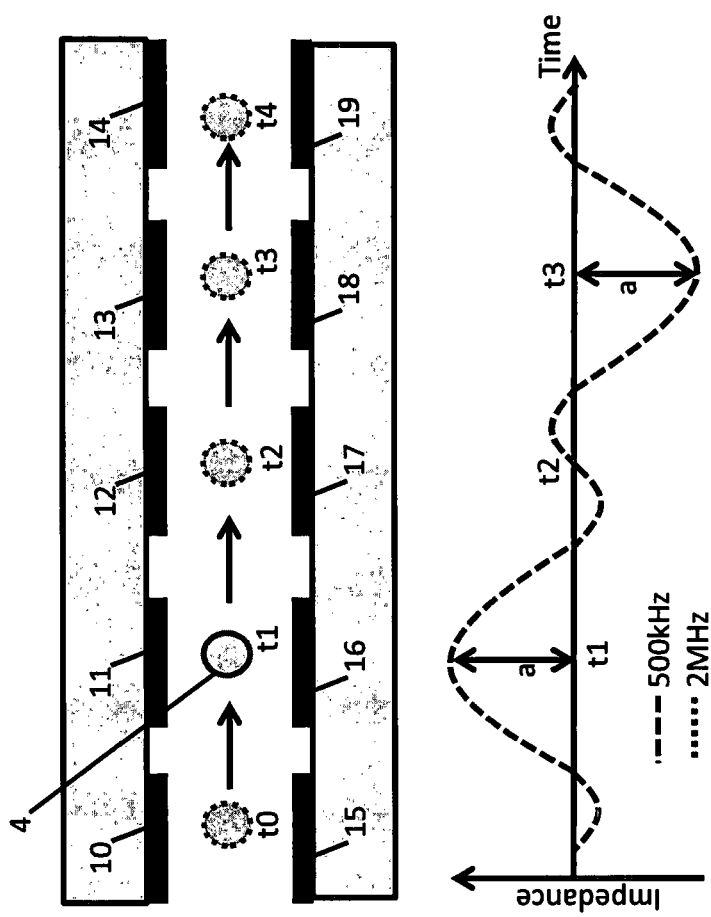
Figure 9. Overview of operation of the new electrode design.

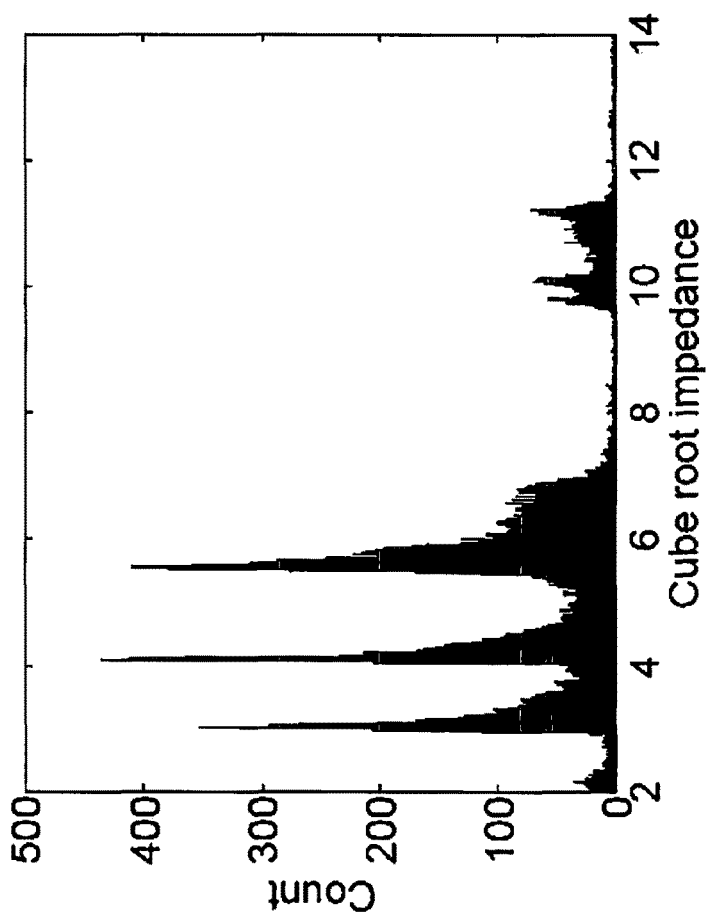
Figure 10. Histogram of a mixture of 3, 4.5, 6 and 10 μm diameter polystyrene beads experimentally measured using the electrode configuration shown in Figures 1-2.

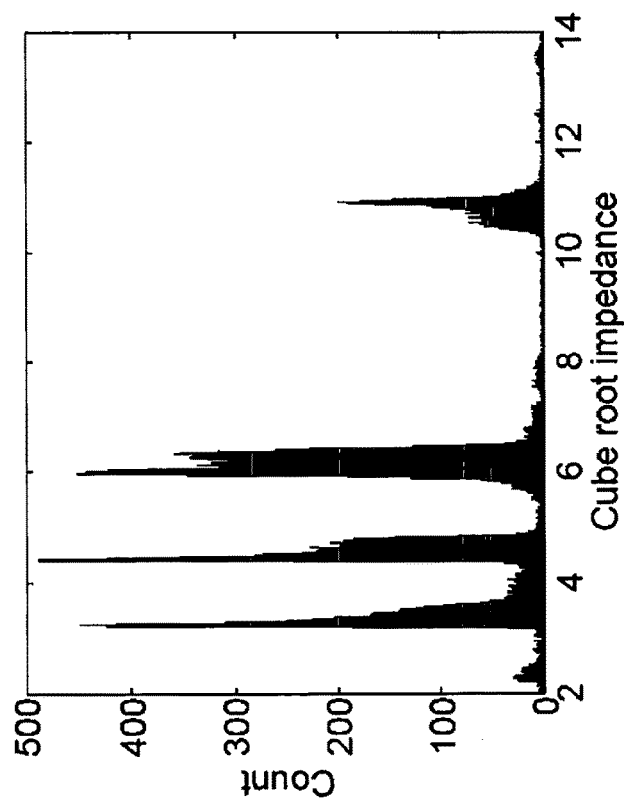
Figure 11. Histogram of a mixture of 3, 4.5, 6 and 10 μm diameter polystyrene beads experimentally measured using the electrode configuration shown in Figures 5-6.

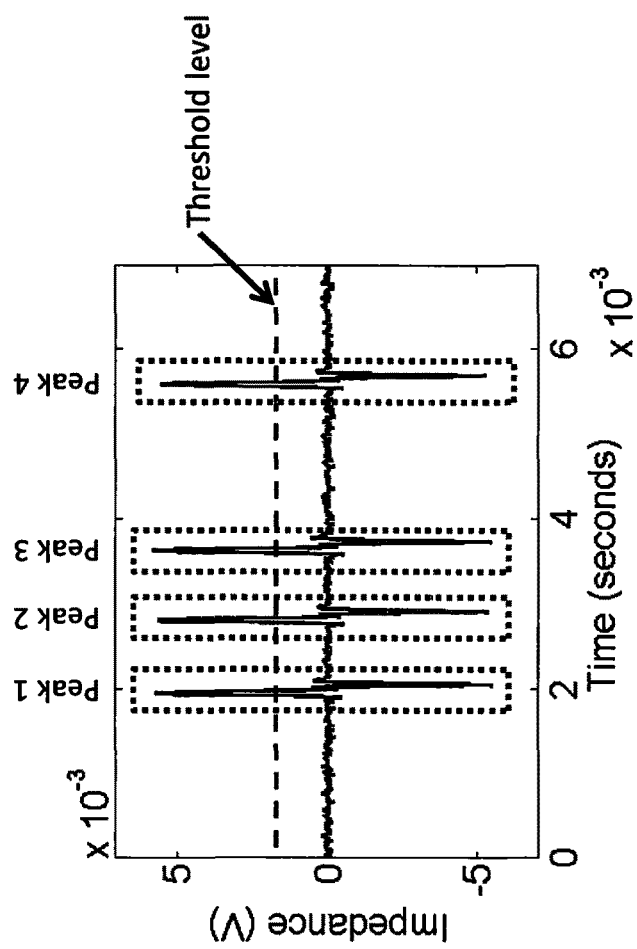
Figure 12. Experimental data showing the impedance signal as 4 particles pass one-by-one through the electrodes. The threshold level is used to detect the 4 particles labelled as peaks 1-4.

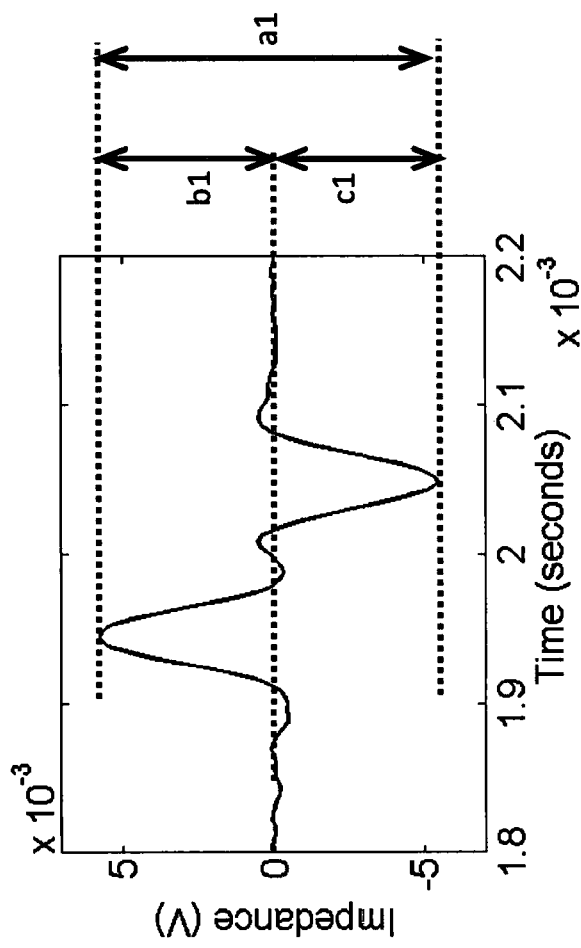
Figure 13. Diagram showing the impedance signal of 1 particle. The heights a1, b1 and c1 are all proportional to the particle volume (size).

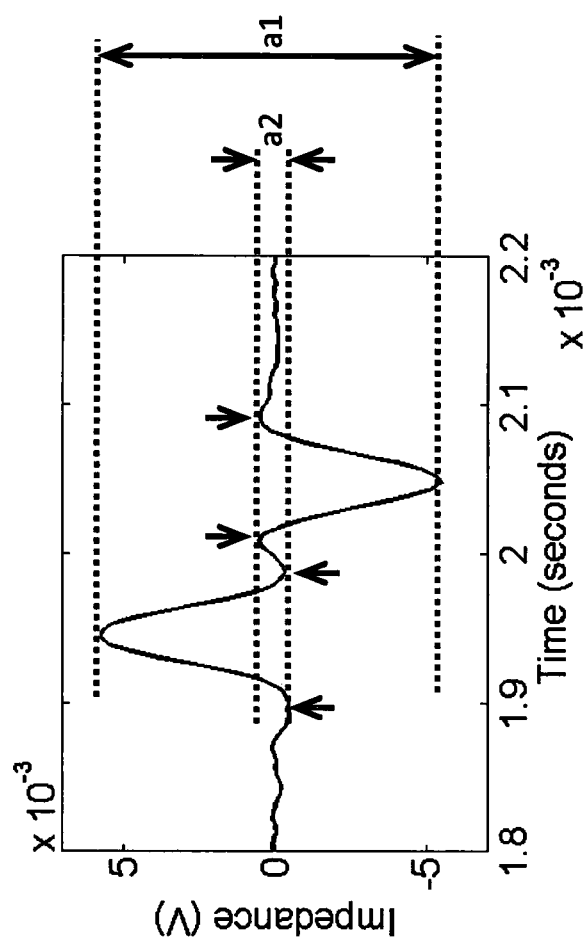
Figure 14. Diagram showing the impedance signal of 1 particle. The ratio of the heights of the primary (a1) and secondary (a2) peaks are used to determine the particle height in the channel.

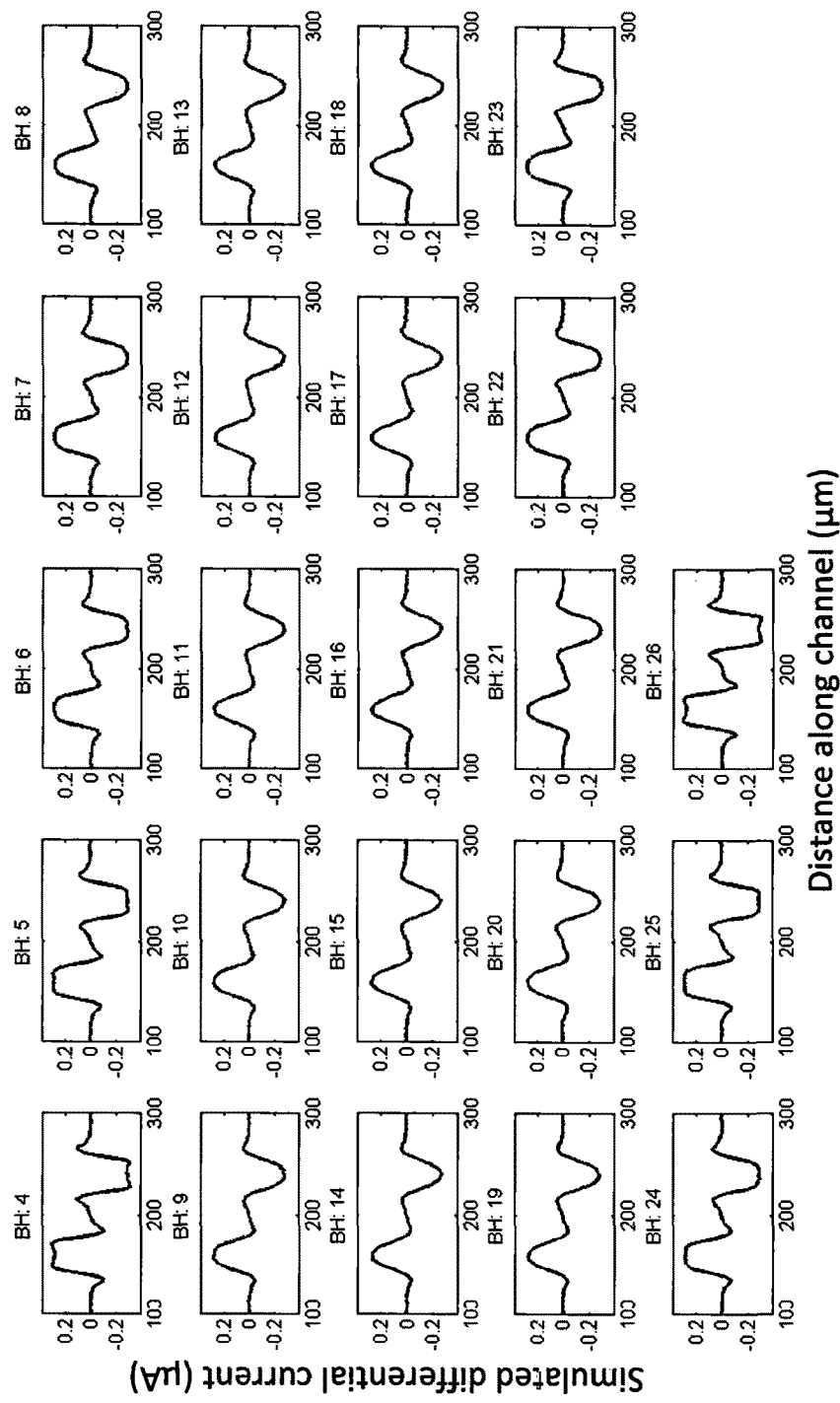
Figure 15. Simulated impedance signals for a 6 μm diameter bead passing through the electrodes shown in Figures 5 and 6 at different heights (BH) in the channel. BH is the distance from the bottom of the channel to the centre of the bead.

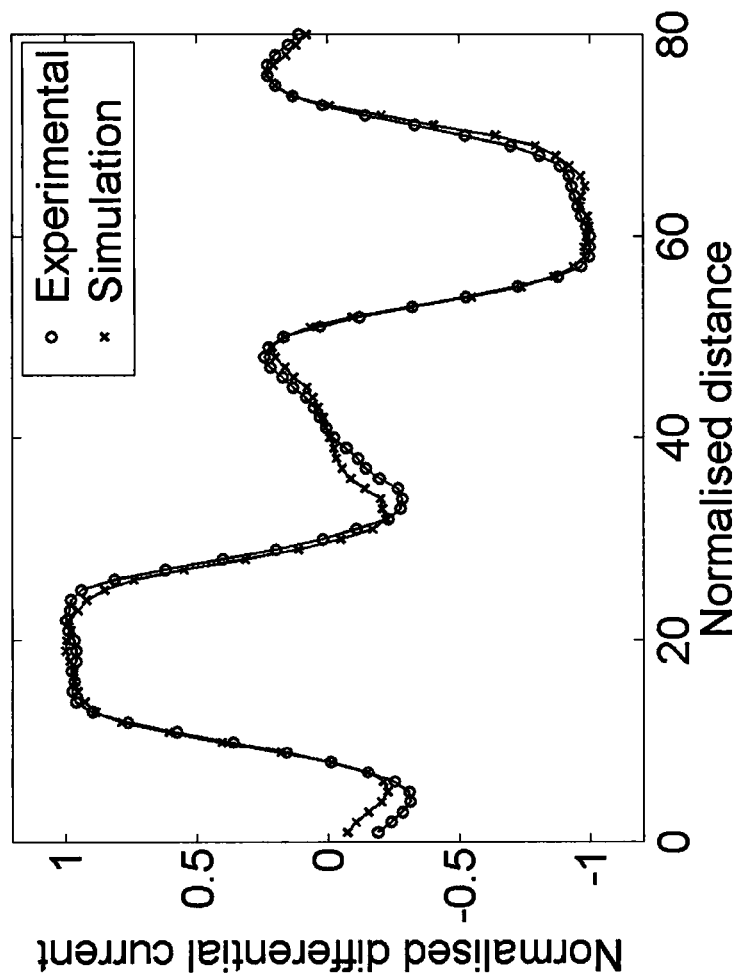
Figure 16. Example of a peak signal from a particle which has passed close to the top of the channel and the best fit simulation spectra.

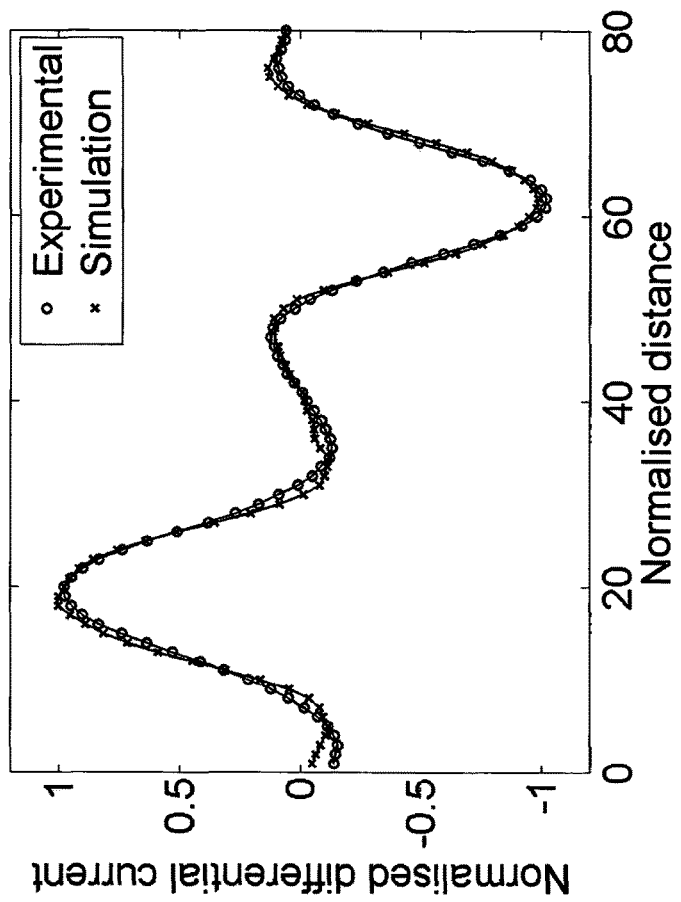
Figure 17. Example of a peak signal from a particle which has passed through the middle of the channel and the best fit simulation spectra.

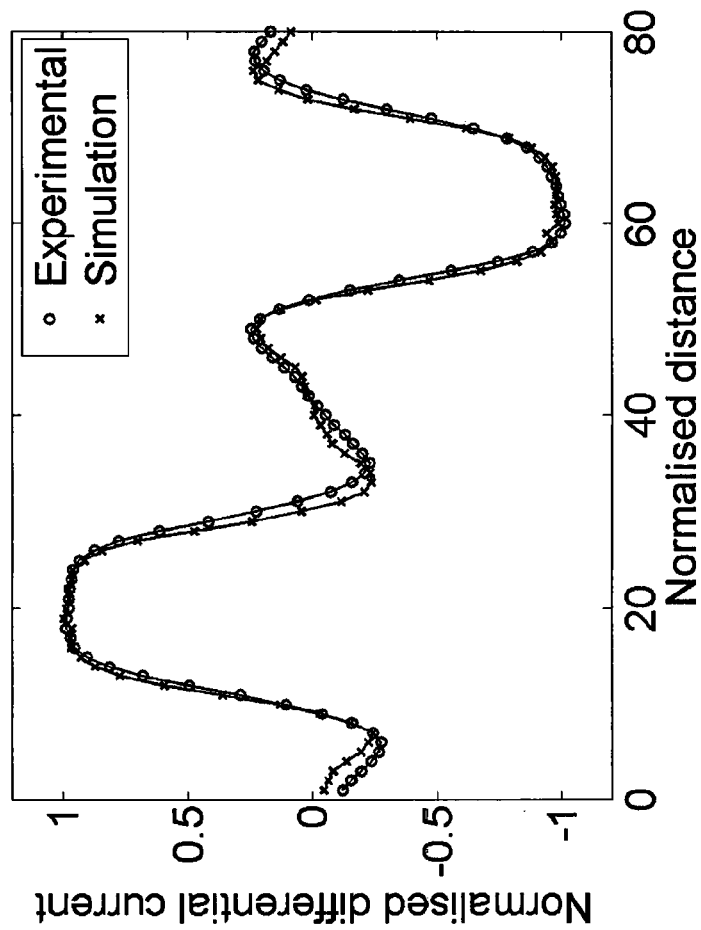
Figure 18. Example of a peak signal from a particle which has passed close to the bottom of the channel and the best fit simulation spectra.

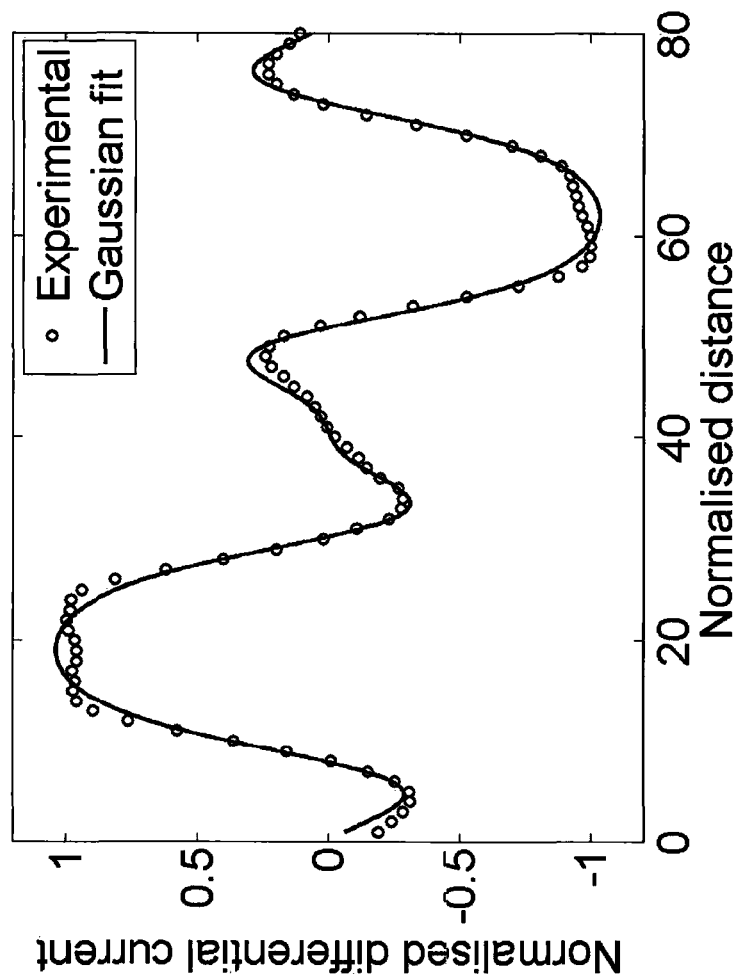
Figure 19. Example of a peak signal from a particle which has passed close to the top of the channel and the best fit sum of gaussians.

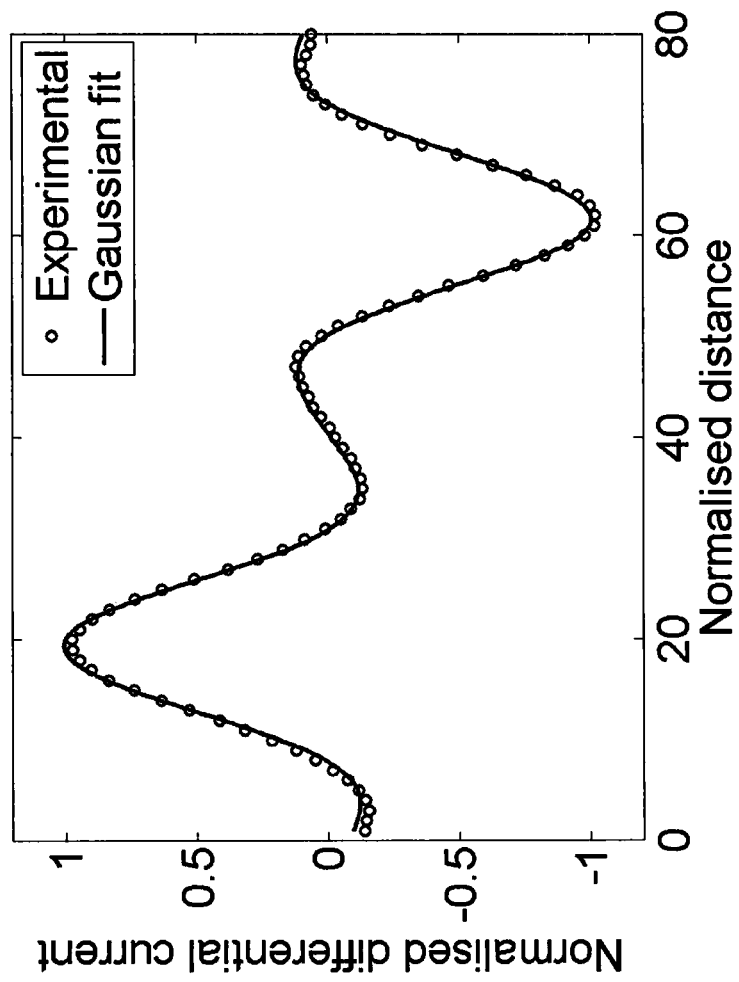
Figure 20. Example of a peak signal from a particle which has passed through the middle of the device and the best fit sum of gaussians.

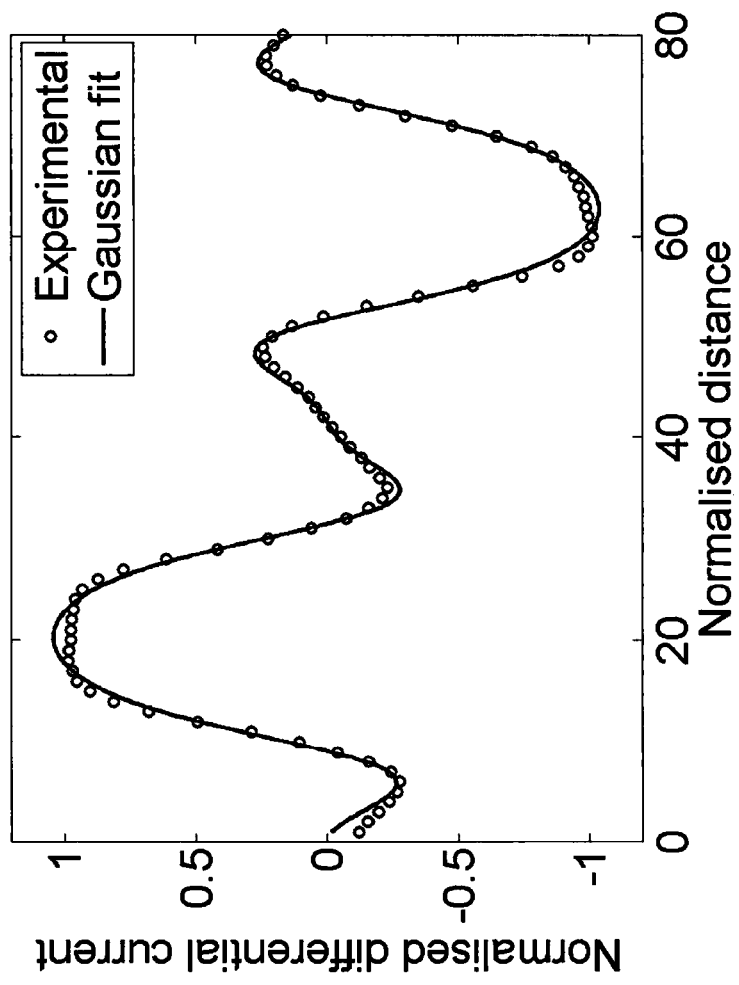
Figure 21. Example of a peak signal from a particle which has passed close to the bottom of the channel and the best fit sum of gaussians.

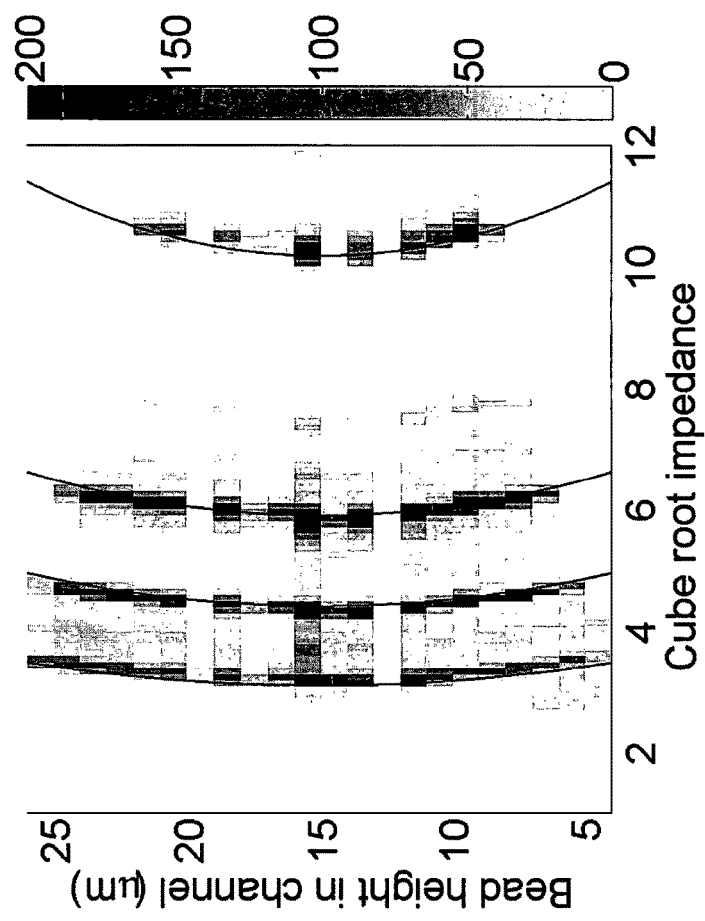
Figure 22. Density plot of the measured impedance of a sample containing 3, 4.5, 6 and 10 μm beads. The bead height within the channel is determined by fitting simulations to each event spectra.

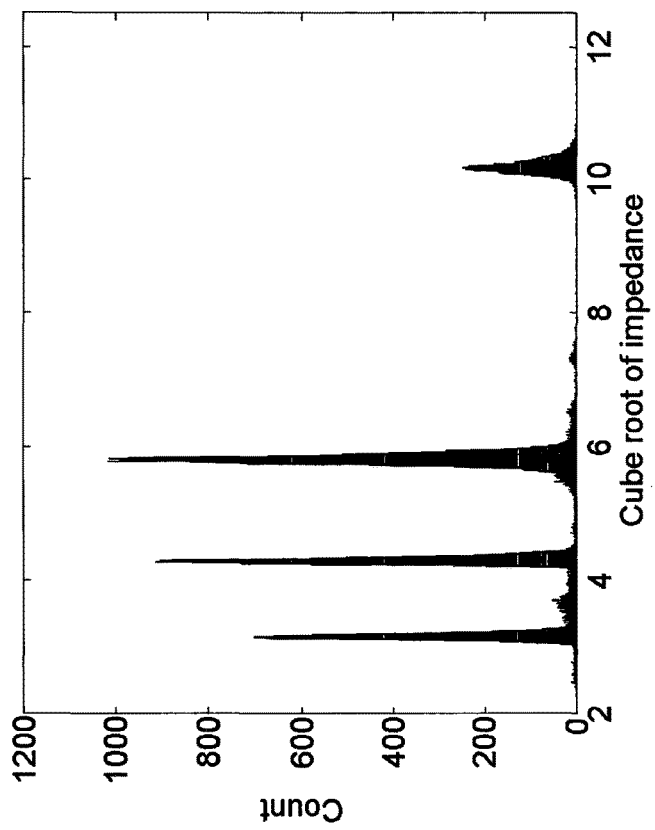
Figure 23. Histogram of the impedance of 3, 4.5, 6 and 10 μm beads after correction for positional dependence by matching the impedance signal directly with simulations.

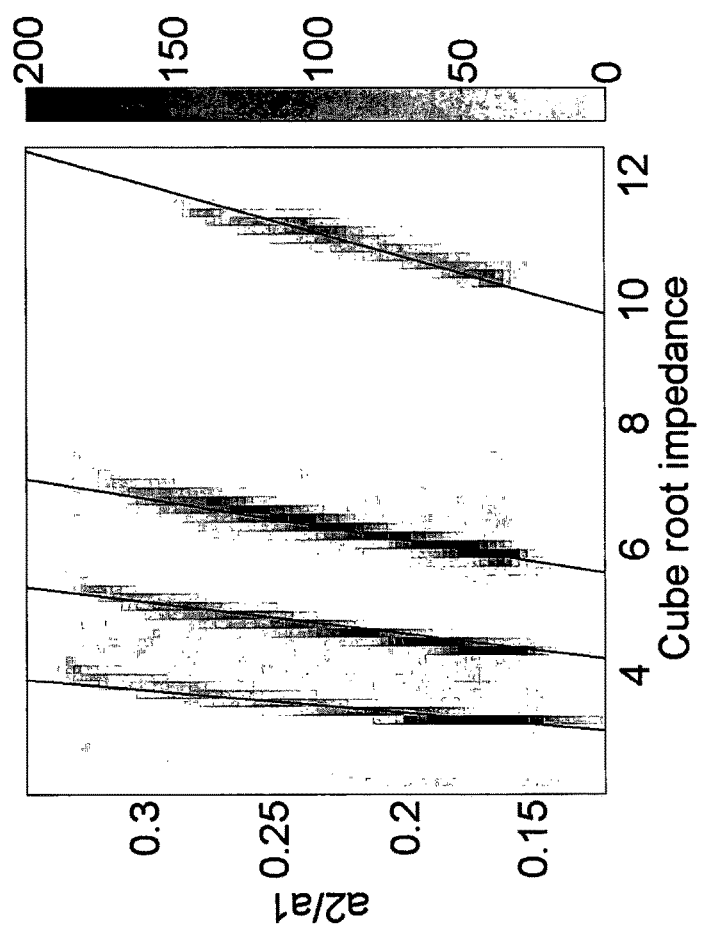
Figure 24. Density plot of the impedance signal plotted against the ratio of the secondary to primary peaks for a mixture of 3, 4.5, 6 and 10 μm diameter beads.

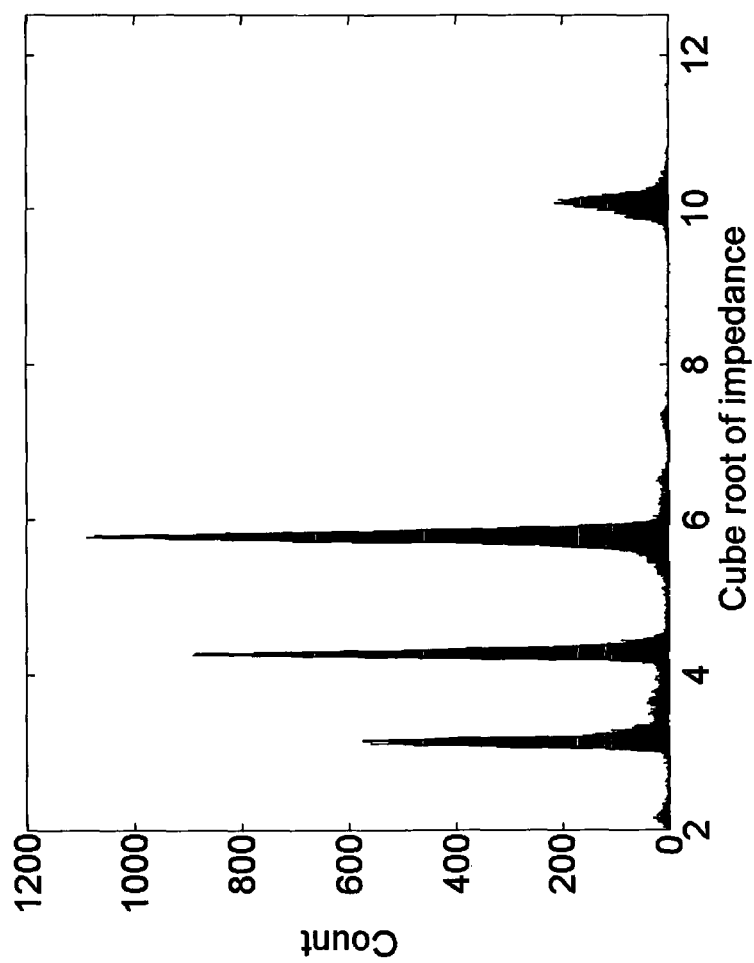
Figure 25. Histogram of the impedance of 3, 4.5, 6 and 10 μm beads after correction for positional dependence by comparing the ratio of the primary to secondary peaks.

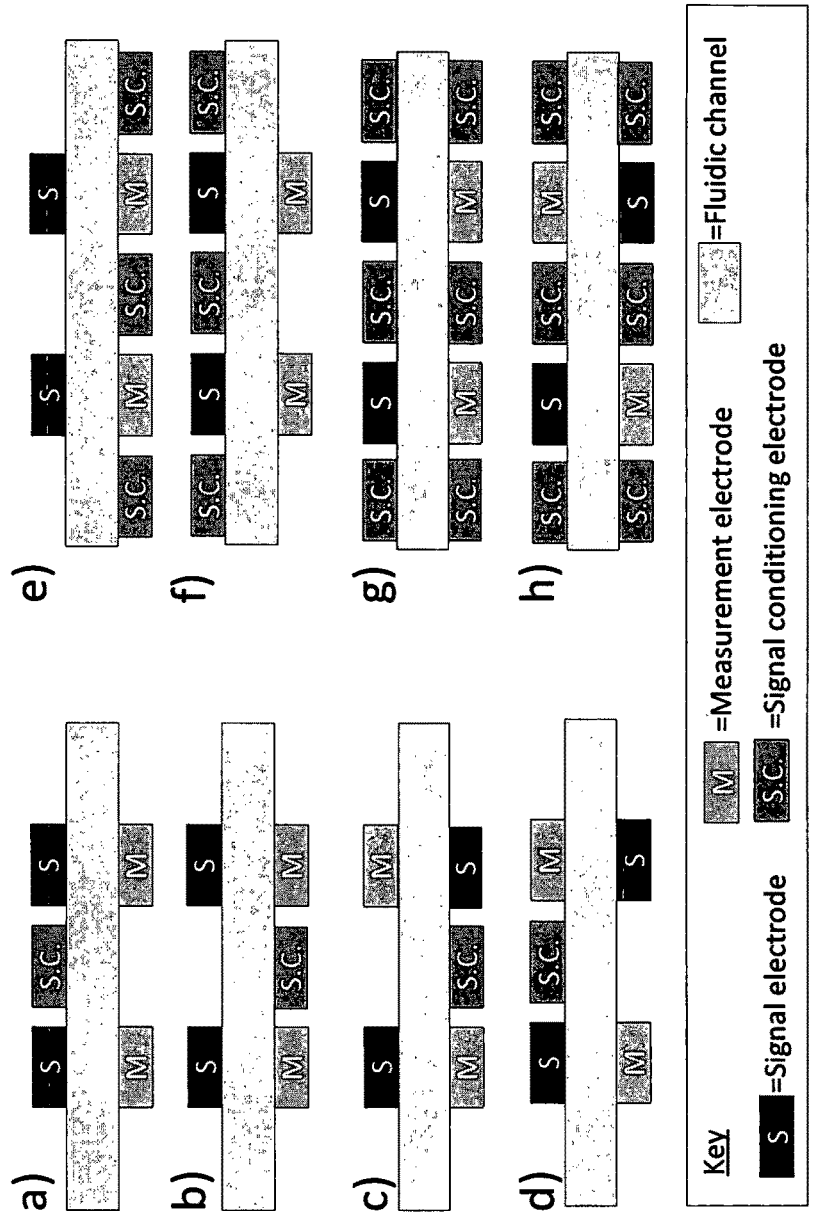
Figure 26a. Different relative positions for signal electrodes, measurement electrodes and signal conditioning electrodes.

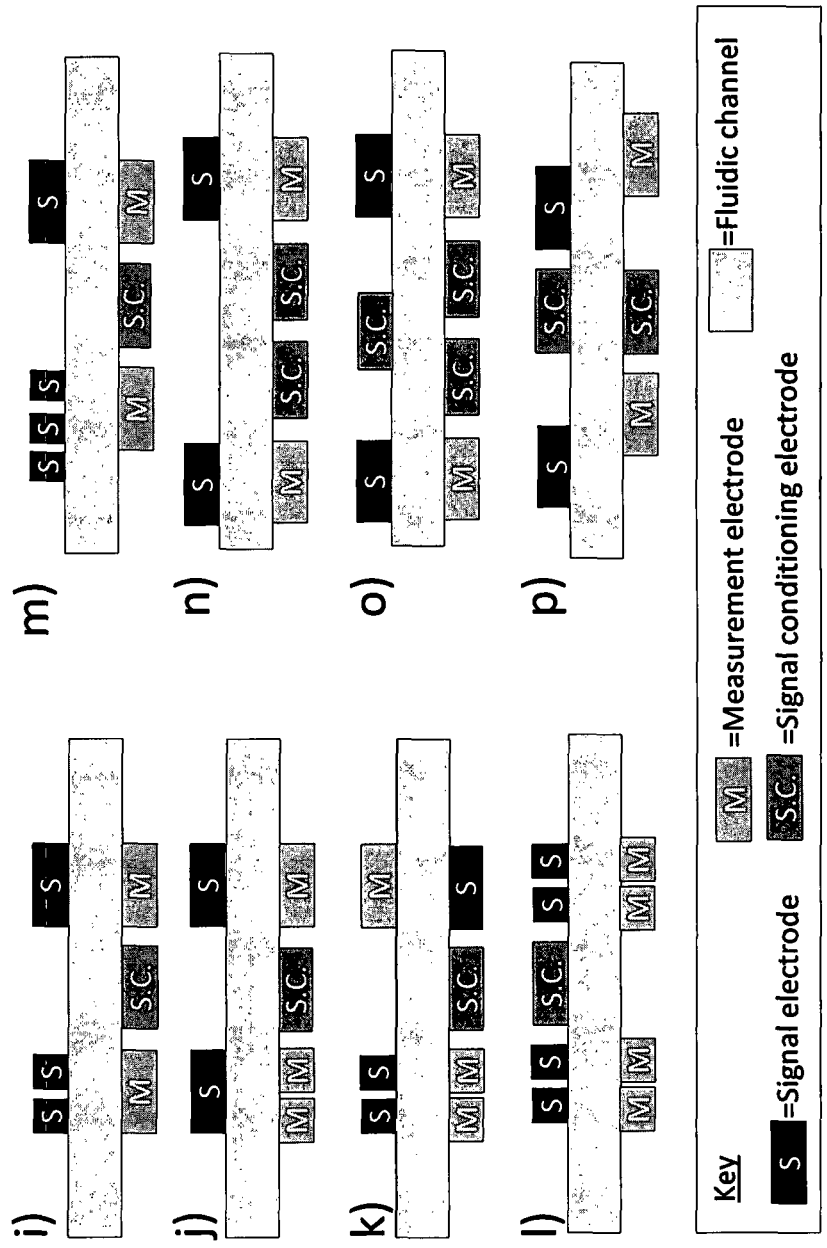
Figure 26b. Different relative positions for signal electrodes, measurement electrodes and signal conditioning electrodes.

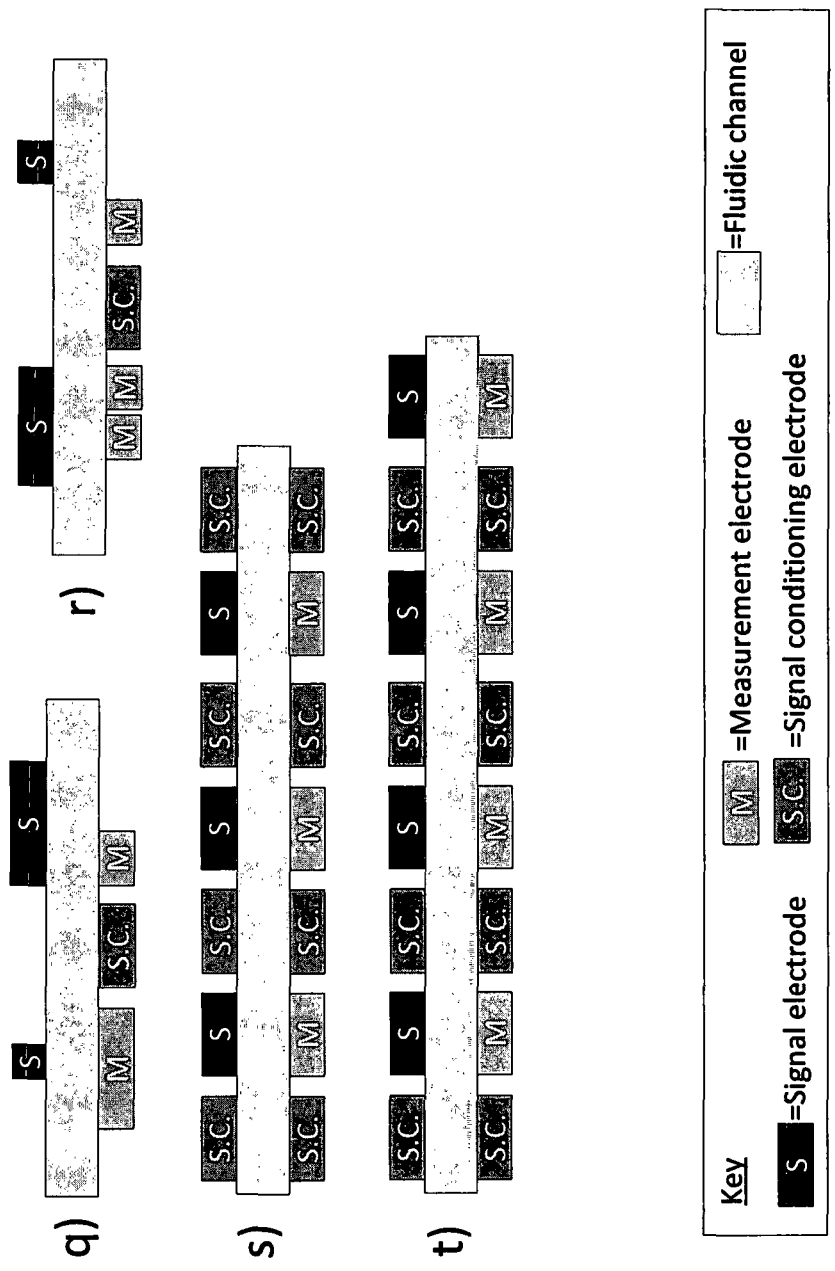
Figure 26c. Different relative positions for signal electrodes, measurement electrodes and signal conditioning electrodes.

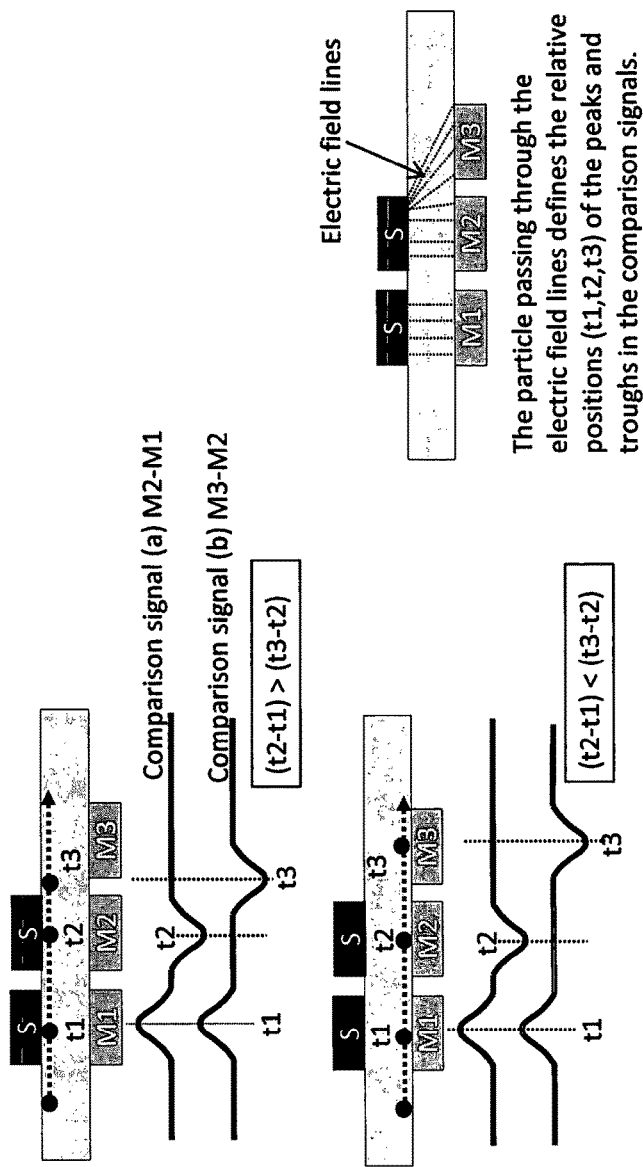
Figure 27. Different steps for measuring electrical signals and generating a comparison signal.

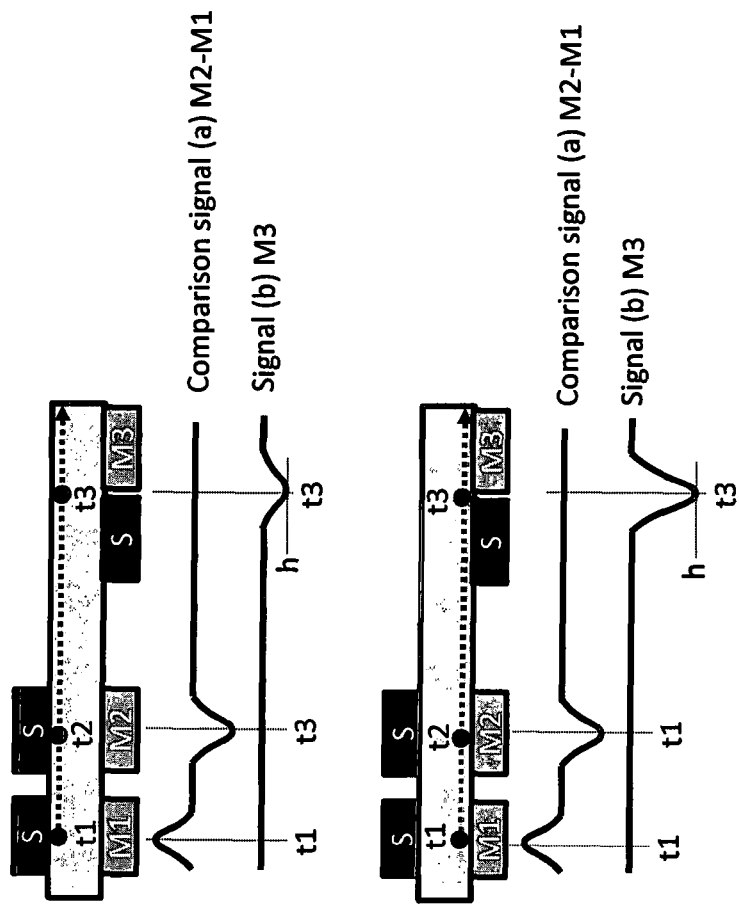
Figure 28. Different steps for measuring electrical signals and generating a comparison signal.

METHOD OF ELECTRICALLY MEASURING THE ELECTRICAL PROPERTIES OF INDIVIDUAL PARTICLES FLOWING IN A LIQUID

This invention relates to a method of electrically measuring the electrical properties of individual particles flowing in a liquid.

Apparatus is known for electrically measuring the electrical properties of individual particles flowing in a liquid. The electrical measurement of individual particles flowing in a liquid is known as microfluidic impedance cytometry. The known apparatus does not provide accurate measurements. More specifically, the known apparatus for electrically measuring individual particles flowing in a liquid comprises of a fluidic channel for receiving a fluid having the individual particles in suspension in the liquid, a first electrode arrangement having a measurement electrode and a signal electrode, and a second electrode pair having a measurement electrode and a signal electrode. The fluidic channel is often known as a microfluidic channel. The first electrode arrangement and the second electrode arrangement are usually miniature measurement electrodes, and they may be fabricated on the top and bottom of the fluidic channel.

In the known apparatus, the individual particles pass in the gap between the first and second electrode arrangements. The individual particles cause a change in electrical current and this change in electrical current is measured and recorded as an impedance signal. A problem exists in that, in the known apparatus, an individual particle travelling close to the electrodes has a higher measured impedance compared to the same sized particle travelling through the centre of the fluidic channel. This higher measured impedance is due to the fact that the particle distorts the electric field between the measurement electrodes, and this causes a difference in current flow between the first and second electrode arrangements. This in turn leads to large measured coefficients of variation in the properties of the particles.

It is an aim of the present invention to obviate or reduce the above mentioned problem.

Accordingly, the present invention provides a method of electrically measuring the electrical properties of individual particles flowing in a liquid, which method comprises:
(i) providing apparatus which is for electrically measuring the individual particles and which has:
 (a) a fluidic channel for receiving a liquid having the individual particles in suspension in the liquid;
 (b) a first electrode arrangement having at least one measurement electrode and at least one signal electrode;
 (c) at least one other electrode arrangement having at least one measurement electrode and at least one signal electrode; and
 (d) at least one signal conditioning electrode;
(ii) providing a flow of the liquid through the fluidic channel;
(iii) applying an electrical signal through the liquid and along a first conduction path between the signal electrode and the measurement electrode of the first electrode arrangement;
(iv) applying an electrical signal through the liquid and along a conduction path between the signal electrode and the measurement electrode of the other electrode arrangement;
(v) comparing the electrical signal between the first and the other conduction paths to generate a comparison signal;
(vi) controlling the potential of the signal conditioning electrode to generate at least one additional feature in the comparison signal;
(vii) detecting an individual particle passing through the apparatus by detecting a feature in the comparison signal of the individual particle, and obtaining at least one output waveform;
(viii) measuring a height-related feature of the output waveform of the individual particle, and generating a first order assessment of the electrical properties of the individual particle; and
(ix), assessing the shape of the additional feature to perform a second order adjustment to the first order assessment of the electrical properties of the individual particle, with the second order adjustment utilising data on a perceived degree of error in the first order assessment based on information on a known relationship between the additional feature and the error in the first order assessment.

The method of the invention is advantageous in providing improved accuracy of measurement. The method of the present invention may be used in a wide variety of technical areas where there is a requirement for high accuracy dielectric measurements of any small particles. Thus, for example, the method of the present invention may be used to measure individual particles in the form of cells, bacteria, phytoplankton, trypanosomes, dust particles, or other appropriate objects. By way of example, it is mentioned that the method of the present invention may be used for a point-of-care full blood count. The counting and discrimination of different cell types is often diagnostically important. Also important is the measuring of the distribution width of populations of cells, which requires a high accuracy measurement. Other examples of uses of the present invention are for platelet measurements, which may be required as part of a point-of-care test for liver fibrosis for patients with liver fibrosis. Still further, the method of the present invention may be used to provide high accuracy measurements of pollen or dust in ice cores, which are needed to date and analyse samples for environmental analysis. Still further, the present invention is easy to operate with various types of apparatus, for example to enable on-the-fly sample pre-processing (including cell labelling or pre-enrichment) for a wide variety of applications.

The method of the invention may be one in which step (ix) comprises comparing the additional feature with a set reference waveforms to find which of the reference waveforms matches the measured output waveform, and then performing the second order adjustment.

The set of reference waveforms may be from simulations of individual particles passing at different positions in the fluidic channel. The set of stored reference waveforms may be obtained from other simulations.

The comparison may be effected using a least-square best fit method, a convolution method, or a correlation numerical method.

The method of the present invention may alternatively be one in which step (ix) comprises identifying at least one specific feature from the additional feature, and comparing this specific feature against a look-up table or a stored formula. The advantage of this is that it may not be necessary to process or store the simulated waveforms. Thus this method of conducting the present invention may compare favourably with the previously above mentioned method for step (ix) which, bearing in mind that 1,000 particles per second may need to be counted for example, may give rise to considerable computerised demands of approach, and may require off-line processing or considerable power to perform real time processing.

The method of the present invention may be one in which the electrical signal in step (iii) is a sine wave. Other electrical signals may be employed.

The method of the present invention may be one in which step (vi) is such that the detected additional feature in the comparison signal is the height of a peak in the output waveform.

The method of the present invention may be one in which step (vi) is such that the detected additional feature in the comparison signal is the height of a trough in the output waveform.

Alternatively, the method of the present invention may be one in which step (vi) is such that the detected additional feature in the comparison signal may be the difference between a primary positive and negative peaks. The detected additional feature of step (vi) of the comparison signal may be other than those specified above.

The method of the present invention may be one in which the second order adjustment of step (ix) based on a knowledge of how both the waveform shape and peak height vary predictably as a function of the distance that the particle passes from one or other of the electrodes in the first and/or other electrode arrangements.

The fluidic channel may be rectilinear in cross section. Thus the fluidic channel may be square in cross section or it may be rectangular in cross section. The fluidic channel may be 1-100 µm×1-100 µm in size. The fluidic channel may be of other measurements. The fluidic channel may also be other than rectilinear in cross section so that, for example, the fluidic channel may be circular in cross section.

The first and other electrode arrangements may be metal electrode arrangements. In this case, the metal electrodes of each of the first and other metal electrode arrangements may be positioned in the fluidic channel. The metal electrodes of each of the first and other metal electrode arrangements may be positioned in the fluidic channel and opposite each other. The metal electrodes of each of the metal electrode arrangements may be similar in size to the particles to be measured for example 1 µm-100 µm wide, for example for biological cells. Other measurements for the metal electrodes may be employed.

Alternatively, the first and other electrode arrangements may be liquid electrode arrangements. The liquid electrode arrangements may be provided in an electrode channel which is additional to the fluidic channel.

Alternatively, the first and other electrode arrangements may be gel electrode arrangements.

The liquid may be an electrolyte and/or an oil. Other types of liquid able to suspend the particles may be employed.

The method of the present invention may be one in which the signal conditioning electrode prevents current flow between the first electrode arrangement and the other electrode arrangement and thereby helps to prevent off-center flow of the individual particles through the fluidic channel whereby the compared signal, for example impedance, of step (v) is of improved accuracy.

The signal conditioning electrode may be positioned between the measurement electrode of the first electrode arrangement and the measurement electrode of the other electrode arrangement. There may be three of the signal conditioning electrodes for the measurement electrodes, with one of the signal conditioning electrodes being positioned on each side of the measurement electrode of the first electrode arrangement and the measurement electrode of the other electrode arrangement.

There may be one of the signal conditioning electrodes positioned between the signal electrode of the first electrode arrangement and the signal electrode of the other electrode arrangement. There may be three of the signal conditioning electrodes for the signal electrodes, with one of the signal conditioning electrodes being positioned on each side of the signal electrode of the first electrode arrangement and the signal electrode of the other electrode arrangement.

The measurement electrodes of the first and other electrode arrangements may be driven by a voltage source, whereby the measured signal is based on a current. The voltage source may be of variable frequency. Alternatively, the measurement electrodes of the first and other electrode arrangements may be driven by a current source, whereby the measured signal is based on a voltage.

The signal conditioning electrode may provide an earth voltage. Alternatively, the signal conditioning electrode may provide a voltage which is that of either of the measurement electrodes of the first and second electrode arrangements.

Embodiments of the invention will now be described solely by way of example and with reference to the accompanying drawings in which:

FIG. 1 is a circuit diagram of known apparatus for electrically measuring individual particles flowing in a liquid;

FIG. 2 is a view like FIG. 1 but shows the apparatus of FIG. 1 in more detail;

FIG. 3 is a circuit diagram of known apparatus for electrically measuring individual particles flowing in a liquid in a guard electrode configuration;

FIG. 4 is a view like FIG. 3 but shows the apparatus of FIG. 3 in more detail;

FIG. 5 is a circuit diagram for electrically measuring individual particles in a liquid with the addition of signal conditioning electrodes;

FIG. 6 is a view like FIG. 5 but shows the apparatus of FIG. 5 in more detail;

FIG. 7 is a simulated variation in particle impedance with position, and shows the variation for the known standard electrode design shown in FIG. 1 and FIG. 2, for the known guard electrode configuration shown in FIG. 3 and FIG. 4, and for the signal conditioning electrode design shown in FIG. 5 and FIG. 6;

FIG. 8 shows a side view of the apparatus in FIGS. 5 and 6 in more detail;

FIG. 9 illustrates individual particles passing through part of the apparatus shown in FIG. 8, and also shows an example signal for the particle positions shown in FIG. 9;

FIG. 10 is a histogram of experimentally measured impedance for a sample containing different sizes of individual particles in a standard 4 electrode configuration as shown in FIGS. 1 and 2;

FIG. 11 is a histogram like that shown in FIG. 13 but obtained with the use of the additional signal conditioning electrodes as shown in FIGS. 5 and 6;

FIG. 12 is a section of experimental data showing the impedance signal over time as 4 particles pass through the electrodes, and also shows a threshold level used to identify the 4 peaks;

FIG. 13 is an obtained signal for an individual particle, showing three heights (a1, b1 and c1) which are each proportional to the volume (size) of the particle;

FIG. 14 is like FIG. 13, but identifies the primary and secondary peaks in the impedance signal;

FIG. 15 shows simulated impedance signals for a 6 µm diameter particle passing through the electrodes shown in FIG. 5 and FIG. 6 at different heights in the channel;

FIG. 16 shows an obtained signal from a particle passing close to the top of the fluidic channel and the best-fit simulated signal from FIG. 15;

FIG. 17 is like FIG. 16 except for a particle passing through the centre of the fluidic channel;

FIG. 18 is like FIG. 16 and FIG. 17 except for a particle passing close to the bottom of the fluidic channel;

FIG. 19 shows an obtained signal from a particle passing close to the top of the fluidic channel and the best-fit sum line of a sum of six Gaussian signals;

FIG. 20 is like FIG. 19 except for a particle passing through the centre of the fluidic channel;

FIG. 21 is like FIG. 19 and FIG. 20 except for a particle passing close to the bottom of the fluidic channel;

FIG. 22 is a density plot of measured impedance of a sample containing individual particles of different sizes, and shows estimated bead height in the channel as found by fitting each experimental peak with simulated peak spectra:

FIG. 23 is a histogram of the impedance of individual particles of different sizes after correction for positional dependence by fitting simulation templates to each peak signal;

FIG. 24 is a density plot of measured impedance of a sample containing individual particles of different sizes, and shows the ratio of the primary peak to secondary peak height (a1 and a2 shown in FIG. 14) as found by fitting each experimental peak with a sum of Gaussians equation;

FIG. 25 is a histogram of the impedance of individual particles of different sizes after correction for positional dependence by fitting a sum of Gaussians equation;

FIGS. 26a-26c show different positions for signal electrodes, measurement electrodes and signal conditioning electrodes in apparatus used in the present invention;

FIG. 27 illustrates a comparison method; and

FIG. 28 illustrates another comparison method.

Referring to FIGS. 1 and 2, there is shown known apparatus 1 for electrically measuring individual particles 4 flowing in a liquid 6. The apparatus 1 comprises a fluidic channel 5 for receiving a liquid 6 having the individual particles 4 in suspension in the liquid 6. The apparatus 1 also comprises a first electrode arrangement 8 having a measurement electrode 16 and a signal electrode 11. The apparatus 1 further comprises another electrode arrangement in the form of a second electrode arrangement 9 having a measurement electrode 18 and a signal electrode 13.

The apparatus 1 is such that the measurement electrodes 16, 18 are connected to an amplifier, whereby individual particles passing between the first and second electrode arrangements 8, 9 cause a change in electrical current which is measured and recorded as an impedance signal. This measurement is effected using current to voltage means 20 connected to the measurement electrode 16 of the first electrode arrangement 8, and current to voltage means 21 connected to the measurement electrode 18 of the second electrode arrangement 19. The two current to voltage means 20, 21 connect to a differential amplifier 22 which provides an output voltage 23. FIG. 1 shows the two current to voltage means 20, 21 and the differential amplifier 22 in block diagram form. FIG. 2 shows in more detail the two current to voltage means 20, 21 and the differential amplifier 22. More specifically, as can be seen in FIG. 2, each current to voltage means 20, 21 comprises a resistor 24 and an operational amplifier 25. The differential amplifier 22 comprises four resistors 26 connected as shown to an operational amplifier 27.

As can be seen from both FIGS. 1 and 2, the signal electrodes 11, 13 of the first and second electrode arrangements 8, 9 are fed with an alternating current voltage source 7.

Hitherto, the apparatus 1 would be operated such that the signal electrodes 11, 13 are driven from the alternating voltage source 7 which may be of variable frequency. The particles 4 pass in the gap 28 between the first and second electrode arrangements 8, 9. The change in electrical current is measured and recorded as an impedance signal. Two electrode arrangements 8, 9 are employed as opposed to just one electrode arrangement to enable a differential mode of operation, which reduces noises and artefacts. However, there are still limitations as to the quality of data provided by the apparatus 1. In particular, this has to do with the fact that the impedance signal depends on the absolute position of the measured individual particle 4 within the detection volume. A particle 4 travelling close to the electrodes of the first and second electrode arrangements 8, 9 has a higher measured impedance compared to the same sized particle 4 travelling through the centre of the fluidic channel 5. This is because the particle 4 distorts the electrical field between the measurement electrode arrangements 8, 9. This particle positional dependence leads to a very large measured coefficient of variation in particle properties, with this very large measured coefficient of variation being much larger than in reality.

In accordance with the method of the present invention, the apparatus shown in FIGS. 1 to 6 is operated such that it provides a method of electrically measuring the electrical properties, for example size, of individual particles flowing in a liquid. The method comprises:

(i) providing the apparatus 1-3 which is for measuring the electrical properties and which is in the form of a microfluidic impedance cytometer 1 having:
  (a) a fluidic channel 5 for receiving a liquid having the individual particles in suspension in the liquid;
  (b) a first electrode arrangement 8 having a measurement electrode 16 and a signal electrode 11; and
  (c) at least one other electrode arrangement in the form of a second electrode arrangement 9 having a measurement electrode 18 and a signal electrode 13;

(ii) providing a flow of the liquid through the fluidic channel 5;

(iii) applying a first electrical signal through the liquid 6 and along a first conduction path between the measurement electrode 16 and the signal electrode 11 of the first electrode arrangement 8;

(iv) applying a second electrical signal through the liquid and along at least one other conduction path in the form of a second conduction path between the measurement electrode 18 and the signal electrode 13 of the second electrode arrangement 9;

(v) comparing the impedance between the first and second conductive paths to generate a comparison signal;

(vi) detecting an individual particle passing through the microfluidic impedance cytometer 1 by detecting a feature of the comparison signal, and obtaining an output waveform;

(vii) measuring a height-related feature of the output waveform, and generating a first order assessment of the size of the individual particle 4; and (viii) assessing the shape of the output waveform to perform a second order adjustment to the first order assessment of the size of the individual particle, with the second order adjustment utilising data, for example stored data, on a perceived degree of error in the first order assessment based on stored information on a known relationship between the waveform shape and the error in the first order assessment.

The above described method of the invention is one in which step (viii) comprises identifying at least one specific feature from the output waveform, and comparing this specific feature against a look-up table or a stored formula. This may enable step (iii) advantageously to be formed without the need to process or store the simulated waveforms.

The high frequency electrical signal of step (iii) may be a sine wave.

The above step (vi) may be such that detected feature of the comparison signal is the height of a peak in the output waveform.

The second order adjustment of step (viii) is based on a knowledge of how both the waveform shape and peak height vary predictably as a function of the distance that the particle passes from one or other of the electrodes in the first and/or second electrode arrangements.

The method of the present invention may also be conducted using the novel apparatus 3 which is shown in FIGS. 5 and 6. FIGS. 5 and 6 are similar to FIGS. 1 and 2 and similar parts have been given the same reference numerals for ease of comparison and understanding. Unlike FIGS. 1 and 2, FIGS. 5 and 6 show apparatus 3 with signal conditioning electrodes.

The apparatus 3 is such that it includes signal conditioning electrodes. More specifically, there is a signal conditioning electrode 17 provided between the measurement electrode 16 of the first electrode arrangement 8, and the measurement electrode 18 of the second electrode arrangement 9. As can be seen from FIGS. 5 and 6, the signal conditioning electrode 17 is one of three signal conditioning electrodes 15, 17, 19 employed for the measurement electrodes 16, 18. The position of the signal conditioning electrodes 15, 17, 19 is such that there is one of the signal conditioning electrodes 15, 17, 19, positioned on each side of the measurement electrode 16 of the first electrode arrangement 8 and the measurement electrode 18 of the second electrode arrangement 9.

The apparatus 3 is such that there is a signal conditioning electrode 12 positioned between the signal electrode 11 of the first electrode arrangement 8 and the signal electrode 13 of the second electrode arrangement 9. As can be seen from FIGS. 5 and 6, the signal conditioning electrode 12 is one of three signal conditioning electrodes 10, 12, 14 employed for the signal electrodes 11, 13. The arrangement of the signal conditioning electrodes 10, 12, 14 is such that there is one of the three signal conditioning electrodes 10, 12, 14 positioned on either side of the signal electrode 11 of the first electrode arrangement 8, and the signal electrode 13 of the second electrode arrangement 9.

The first and second electrode arrangements 8, 9 are metal electrode arrangements. As can be seen from FIGS. 5 and 6, the first and second metal electrode arrangements 8, 9 are positioned in the fluidic channel 5 and such that the metal electrodes of each of the first and second metal electrode arrangements 8, 9 are positioned in the fluidic channel 5 and opposite each other. By way of example only, it is mentioned that the metal electrodes of each of the first and second electrode arrangements 8, 9 may be 20 µm-40 µm wide.

The fluidic channel 5 is rectilinear in cross section. More specifically, the fluidic channel 5 is square in cross section. By way of example only, it is mentioned that the fluidic channel 5 may typically be 40 µm by 40 µm.

The signal conditioning electrodes 10, 12, 14, 15, 17, 19 may provide an earth voltage. In an alternative embodiment of the invention, the signal conditioning electrodes 10, 12, 14, 15, 17, 19 may provide a voltage which is that of either of the measurement electrodes 16, 18 of the first and second electrode arrangements 8, 9.

Also by way of non-limiting example, it is mentioned that the measurement electrodes 16, 18 are at virtual ground, the signal electrodes 11, 13 may be between 1 and 20 volts, and the signal conditioning electrodes 10, 12, 14, 15, 17, 19 are at 0 volts.

FIG. 3 and FIG. 4 show how the fluidic channel 5 would look using known guard electrodes instead of the signal conditioning electrodes. The known guard electrodes are identified by the same numbers as the signal conditioning electrodes but with the addition of the letter "a".

For ease of comparison and understanding, the various parts shown in FIGS. 3 and 4 have been given the same reference numerals and the same non-limiting example measurements and the same non-limiting voltage values for the signal electrodes, the measurement electrodes, and the signal conditioning electrodes/guard electrodes.

Use of the signal conditioning electrodes 10, 12, 14, 15, 17, 19 is different from the use of the guard electrodes 10a, 12a, 14a, 15a, 17a, 19a. The signal conditioning electrodes 10, 12, 14, 15, 17, 19 are held at the same voltage as the measurement electrodes 16, 18. In contrast, at least some of the guard electrodes 10a, 12a, 14a, 15a, 17a, 19a shown in the apparatus 2 of the present invention will not be at the same voltage as their closest measurement electrode 16, 18. It is believed to be highly unexpected and very counter-intuitive to realise that it is beneficial to hold all the signal conditioning electrodes 10, 12, 14, 15, 17, 19 at the same voltage as one another. With the guard electrodes 10a, 12a, 14a, 15a, 17a, 19a, the field lines are nicely parallel. However, with the signal conditioning electrodes 10, 12, 14, 15, 17, 19, the field lines diverge from each of the signal electrodes 11, 13, which would be expected to give very poor results. From a consideration of the cross-path electrical flows possible due to blockage by an individual particle 4, it has been appreciated that this is not the case. The signal conditioning electrodes 10, 12, 14, 15, 17, 19 advantageously prevent the first and second electrode arrangements 8, 9 interfering during the passage of an individual particle 4 through the gap 28 in the fluidic channel 5.

FIG. 7 shows a simulated variation in impedance of individual particles 4 with position, in the fluidic channel 5 for the known apparatus 1 shown in FIGS. 1 and 2, the known apparatus 2 shown in FIGS. 3 and 4 and the apparatus 3 shown in FIGS. 5 and 6. It will be seen from FIG. 7 that the use of the signal conditioning electrodes 10, 12, 14, 15, 17, 19 will give substantially less variation in particle impedance with position than is achieved with the use of the guard electrodes 10a, 12a, 14a, 15a, 17a, 19a.

FIG. 8 shows an overview of operation of apparatus 30 of the apparatus 2. The apparatus 30 is such that it has an fluidic channel 31 formed between two layers of glass 30, 32. The two layers of glass 30, 32 are separated by an epoxy-based negative photoresist known as SU-8. , The SU-8 layer 33 defines the height of the fluidic channel 31. By way of non-limiting example it is mentioned that the glass layers 30, 32 may be 1 mm thick, and the layer 33 may be 40 µm thick. Also by way of non-limiting example, it is mentioned that the fluidic channel 31 may be such that it is 40 µm wide, and may have electrodes 10-19 which are 30 µm wide and separated by a gap 66 which is 10 µm wide.

As shown in FIG. 8, individual particles 4 are in a liquid 6 in a sample container 35. The sample container 35 comprises a piston 36 for forcing the liquid 6 through an outlet 37 in the sample container 35. The electrodes 16, 18 are measurement electrodes which are connected to a current to voltage amplifier 21 which in turn is connected to a differential amplifier 22. When the liquid 6 with the individual particles 4 has passed through the fluidic channel 54, the liquid 6 is passed as a waste outlet 38.

In operation of the apparatus 30, the solution of particles 4 to be measured is driven through the apparatus 30. The liquid 6 is diluted such that only one particle 4 is between the electrodes 10-19 at any time. An AC voltage is applied to the top two signal electrodes 11, 13. The difference in current passing through the bottom two measurement electrodes 16, 18 is measured as impedance.

FIG. 9 shows that as a particle 4 passes between the electrodes 10-19, from t=t0 to t4, the impedance signal goes from positive and then negative. The maximum peak of the signal is shown as a1, and this maximum peak is equal to the minimum of the trough, shown as a2. The maximum of the signal a1 is recorded, and is proportioned to the volume (size) of the particle 3.

FIG. 10 is a histogram of experimentally measured impedance of a sample containing 3, 4.5, 6 and 10 μm diameter polystyrene beads measured using apparatus 1 of the type shown in FIGS. 1 and 2.

FIG. 11 is a similar histogram to that shown in FIG. 10 but FIG. 11 shows the histogram obtained using apparatus similar to the apparatus 3 shown in FIGS. 5 and 6.

FIG. 12 is a section of experimental data showing the impedance signal over time as particles 4 pass through the electrodes. Also shown is a threshold level used to identify the 4 peaks each corresponding to a single particle 4.

FIG. 13 is an obtained signal for an individual particle 4, showing three heights (a1, b1 and c1) which are each proportional to the volume (size) of the particle.

FIG. 14 is like FIG. 13, but identifies primary and secondary peaks in the impedance signal.

FIG. 15 shows simulated impedance signals for a 6 μm diameter particle passing through the electrodes shown in FIG. 5 and FIG. 6 at different heights in the channel.

FIG. 16 shows an obtained signal from a particle passing close to the top of the fluidic channel and the best-fit simulated signal from FIG. 15.

FIG. 17 is like FIG. 16 except for a particle passing through the centre of the fluidic channel.

FIG. 18 is like FIG. 16 and FIG. 17 except for a particle passing close to the bottom of the fluidic channel.

FIG. 19 shows an obtained signal from a particle passing close to the top of the fluidic channel and the best-fit sum line of a sum of six Gaussians.

FIG. 20 is like FIG. 19 except for a particle passing through the centre of the fluidic channel.

FIG. 21 is like FIG. 19 and FIG. 20 except for a particle passing close to the bottom of the fluidic channel.

FIG. 22 is a density plot of the measured impedance of a sample containing 3, 4.5, 6 and 10 μm beads. The bead height within the fluidic channel 4 is determined by fitting simulations to each event spectra.

FIG. 23 is a histogram of the impedance of individual particles of different sizes after correction for positional dependence by fitting simulation templates to each peak signal.

FIG. 24 is a density plot of measured impedance of a sample containing individual particles of different sizes, and shows the ratio of the primary peak to secondary peak height (a1 and a2 shown in FIG. 14) as found by fitting each experimental peak with a sum of Gaussians equation.

FIG. 25 is a histogram of the impedance of individual particles of different sizes after correction for positional dependence by fitting a sum of Gaussians equation.

In another embodiment of the method of the present invention, there may be employed a signal processing algorithm that matches measured impedance signals against a template in order to obtain an estimate of the position of each individual particle 4 as the individual particle 4 passes through the fluidic channel 5. In this case, the apparatus shown in FIGS. 5 and 6 may comprise compensation means for using the estimate to compensate obtained electrical signals for the off-centre individual particles and thereby further to increase achieved measurement accuracy of the individual particles. The template used may be one that provides fluctuations obtained using simulation.

The use of a signal processing algorithm thus enables a further improvement in measurements. This may be done by matching the measured impedance signals against the template functions obtained using the simulations (FIG. 15). This provides an estimate of the position of each individual particle 4 as it passes through the fluidic channel 5. This information is then used to further reduce particle positional dependence and to increase the measurement accuracy.

By way of example, each individual event spectra in the data set of FIG. 11 was compared with a set of templates shown in FIG. 15 which were obtained using simulations. This provided an estimate of height for each individual bead 4 as the individual bead 4 passed through the fluidic channel 5. The measured impedance was plotted against the estimated bead height shown in FIG. 22, and shows that individual particles 4 travelling close to the electrodes have a slightly higher impedance signal compared to those travelling through the centre of the fluidic channel 5 (bead height=15 μm). FIG. 22 also shows that this function can be approximated using a polynomial, which is then used to correct for the positional dependence. The correction factor is based on the estimated bead height within the channel and corrects for particle positional dependence.

FIG. 23 shows the data presented in FIG. 11 but after correction for position using the signal processing algorithm. The mean and standard deviation, as calculated from a best-fit Gaussian, is compared to the manufacturer's data in the following table.

| Nominal Diameter (μm) | Manufacturer's data | | | Experimental data | | |
| --- | --- | --- | --- | --- | --- | --- |
| | Diameter (μm) | S. dev. | C.V. | Diameter (μm) | S. dev. | C.V. |
| 3 | 3.11 | 0.088 | 2.83 | 3.15 | 0.048 | 1.53 |
| 4.5 | 4.42 | 0.172 | 3.89 | 4.29 | 0.050 | 1.16 |
| 6 | 6.07 | 0.193 | 3.18 | 5.80 | 0.077 | 1.33 |
| 10 | 10.17 | 0.304 | 2.99 | 10.16 | 0.100 | 0.98 |

By way of example, a sum of Gaussians equation was fitted to each individual event spectra in the data set of FIG. 11 to find the ratio of the primary to secondary peak heights illustrated in FIG. 14. This provided an estimate of height for each individual bead 4 as the individual bead 4 passed through the fluidic channel 5. The measured impedance was plotted against the ratio of the primary to secondary peaks shown in FIG. 24. and shows that individual particles with a higher secondary peak compared to the primary peak (a2/a1=0.3) have a slightly higher impedance signal compared to those with a smaller ratio (a2/a1=0.1). A smaller a2/a1 ratio corresponds to particles passing through the centre of the fluidic channel 5. A higher a2/a1 ratio corresponds to particles passing close to the electrodes (top or bottom of the channel) due to consideration of the cross-flow currents. FIG. 24 also shows that this function can be approximated using a straight line, which is then used to correct for the positional dependence. The correction factor is based on the estimated bead height within the channel which is estimated from the ratio of the primary to secondary peaks and corrects for off-centre particles.

FIG. 25 shows the data presented in FIG. 11 but after correction for position using the signal processing algorithm. The mean and standard deviation, as calculated from a best-fit Gaussian, is compared to the manufacturer's data in the following table.

| Nominal Diameter (µm) | Manufacturer's data | | | Experimental data | | |
|---|---|---|---|---|---|---|
| | Diameter (µm) | S. dev. | C.V. | Diameter (µm) | S. dev. | C.V. |
| 3 | 3.11 | 0.088 | 2.83 | 3.13 | 0.055 | 1.77 |
| 4.5 | 4.42 | 0.172 | 3.89 | 4.28 | 0.050 | 1.16 |
| 6 | 6.07 | 0.193 | 3.18 | 5.78 | 0.074 | 1.28 |
| 10 | 10.17 | 0.304 | 2.99 | 10.07 | 0.110 | 1.09 |

FIGS. 26a, 26b and 26c show different relative positions for the signal electrodes, measurement electrodes and signal conditioning electrodes.

FIG. 27 shows the following three steps for measuring electrical signals and generating a comparison signal.

Step 1: Measure the electrical signals flowing into M1 and M2 and generate a comparison signal (a). This is a first order assessment of the electrical properties of the particle.

Step 2: Measure the signals flowing into M2 and M3 and generate a comparison signal (b).

Step 3: Apply a second order assessment/correction to the comparison signal in step 1 based on the time between peak and trough in step 1 (time t2-time t1), compared to the time between peak and trough in step 2 (t3-t2).

FIG. 28 shows the following three steps for measuring electrical signals and generating a comparison signal.

Step 1: Measure the electrical signals flowing into M1 and M2 and generate a comparison signal (a). This is a first order assessment of the electrical properties of the particle.

Step 2: Measure the electrical signal M3.

Step 3: Apply a second order assessment/correction to the comparison signal in step 1 based on a height-related feature (for example the height h of the trough at t3) from step 2.

The method of the present invention enables simple microfluidic impedance analysis to operate without sheath flow particle positioning. The method of the present invention is able to provide multi-frequency analysis, and it can process small volumes, and can operate continuously, integrated with microfluidic continuous sample pre-processing if needed.

It is to be appreciated that the embodiments of the invention described above with reference to the accompanying drawings have been given by way of example only and that modifications may be effected. Thus, for example, instead of using metal electrodes in the first and at least one other electrode arrangements, 8, 9, the method of the present invention may be implemented use liquid electrodes or gel electrodes. The signal electrodes 11, 13 in the first and the other electrode arrangements 8, 9 may be driven by a current source, with the measured signal being based on a voltage measurement. If the spacing between the measurement electrodes on the one hand and the signal electrode on the other hand is increased sufficiently, then, for example, twice the amount of signal conditioning may be employed between the measurement electrodes and/or the signal electrodes. The end signal conditioning electrodes 10, 14, 15, 19 may be omitted. Also, the electrodes need not be on the same wall as shown and one arrangement of electrodes could be polarity reversed, this being because the arrangements are electrically independent due to the use of the central signal conditioning electrodes 12, 17. Individual components shown in the drawings are not limited to use in their drawings and they may be used in other drawings and in all aspects of the invention.

The invention claimed is:

1. A method of electrically measuring the electrical properties of individual particles flowing in a liquid, which method comprises:
   (i) providing an apparatus which is for electrically measuring the individual particles and which has:
      (a) a fluidic channel for receiving a liquid having the individual particles in suspension in the liquid;
      (b) a first electrode arrangement having at least one measurement electrode and at least one signal electrode;
      (c) at least one other electrode arrangement having at least one measurement electrode and at least one signal electrode;
      (d) at least one signal conditioning electrode; and
      (e) wherein each signal conditioning electrode is adjacent to at least one of the electrode arrangements;
   (ii) providing a flow of the liquid through the fluidic channel;
   (iii) applying an electrical signal through the liquid and along a first conduction path between the signal electrode and the measurement electrode of the first electrode arrangement;
   (iv) applying an electrical signal through the liquid and along a conduction path between the signal electrode and the measurement electrode of the other electrode arrangement;
   (v) comparing the electrical signal between the first and the other conduction paths to generate a comparison signal;
   (vi) controlling in a non-random manner the potential of each signal conditioning electrode to generate at least one additional feature in the comparison signal for each adjacent measurement electrode;
   (vii) detecting an individual particle passing through the apparatus by detecting a feature in the comparison signal of the individual particle, and obtaining at least one output waveform;
   (viii) measuring a height-related feature of the output waveform of the individual particle, and generating a first order assessment of the electrical properties of the individual particle; and
   (ix) assessing the ratio of the height or position of the additional feature generated in step (vi) to the feature in the comparison signal detected in step (vii) to perform a second order adjustment to the first order assessment of the electrical properties of the individual particle generated in step (viii), with the second order adjustment utilizing data on a perceived degree of error in the first order assessment based on information on a known dependence between the additional feature and the error in the first order assessment.

2. A method according to claim 1 in which step (ix) comprises comparing the additional feature with a set of reference waveforms to find which of the reference waveforms matches the measured output waveform, and then performing the second order adjustment.

3. A method according to claim 2 in which the set of reference waveforms is from simulations of individual particles passing at different positions in the fluidic channel.

4. A method according to claim 3 in which the comparison is effected using a least-square best fit method, a convolution method, or a correlation numerical method.

5. A method according to claim 2 in which step (ix) comprises identifying at least one specific feature from the additional feature, and comparing this specific feature against a look-up table or a formula.

6. A method according to claim 1 in which the electrical signal of step (iii) is a sine wave.

7. A method according to claim 1 in which step (vi) is such that the detected additional feature in the comparison signal is the height of a peak in the output waveform.

8. A method according to claim 1 in which the second order adjustment of step (ix) is based on a knowledge of how both the waveform shape and peak height vary predictably as a function of the distance that the particle passes from one or other of the electrodes in the first and/or other electrode arrangements.

9. A method according to claim 1 in which the fluidic channel is rectilinear in cross section.

10. A method according to claim 1 in which the first and other electrode arrangements are metal electrode arrangements.

11. A method according to claim 10 in which the metal electrodes of each of the first and other metal electrode arrangements are positioned in the fluidic channel.

12. A method according to claim 11 in which the metal electrodes of each of the first and other metal electrode arrangements are positioned in the fluidic channel and opposite each other.

13. A method according to claim 1 in which the first and other electrode arrangements are liquid electrode arrangements.

14. A method according to claim 13 in which the liquid electrode arrangements are provided in an electrode channel which is additional to the fluidic channel.

15. A method according to claim 1 in which the first and other electrode arrangements are gel electrode arrangements.

16. A method according to claim 1 in which the signal conditioning electrode prevents current flow between the first electrode arrangement and the other electrode arrangement and thereby helps to prevent off-centre flow of the individual particles through the fluidic channel whereby the compared signal of step (v) is of improved accuracy.

17. A method according to claim 16 in which the signal conditioning electrode is positioned between the measurement electrode of the first electrode arrangement and the measurement electrode of the other electrode arrangement.

18. A method according to claim 16 in which the signal conditioning electrode provides an earth voltage.

19. A method according claim 16 in which the signal conditioning electrodes provide a voltage which is that of either of the measurement electrodes of the first and other electrode arrangements.

20. A method according to claim 1 in which the measurement electrodes of the first and other electrode arrangements are driven by (a) a voltage source, whereby the measured signal is based on a current, or (b) a current source, whereby the measured signal is based on a voltage.

* * * * *